(12) United States Patent
Hossainy

(10) Patent No.: US 9,878,169 B2
(45) Date of Patent: Jan. 30, 2018

(54) PIEZOELECTRIC MEDICAL IMPLANT

(71) Applicants:ABBOTT CARDIOVASCULAR SYSTEMS INC., Santa Clara, CA (US); Syed Hossainy, Hayward, CA (US)

(72) Inventor: Syed Hossainy, Hayward, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 117 days.

(21) Appl. No.: 14/650,818

(22) PCT Filed: Dec. 18, 2013

(86) PCT No.: PCT/US2013/076266
§ 371 (c)(1),
(2) Date: Jun. 9, 2015

(87) PCT Pub. No.: WO2014/100259
PCT Pub. Date: Jun. 26, 2014

(65) Prior Publication Data
US 2016/0184595 A1    Jun. 30, 2016

Related U.S. Application Data

(60) Provisional application No. 61/738,517, filed on Dec. 18, 2012.

(51) Int. Cl.
*A61N 1/375* (2006.01)
*A61N 1/378* (2006.01)
(Continued)

(52) U.S. Cl.
CPC .............. *A61N 1/3756* (2013.01); *A61F 7/12* (2013.01); *A61M 39/0247* (2013.01);
(Continued)

(58) Field of Classification Search
CPC .. A61N 1/3756; A61N 1/3785; A61N 1/3627; A61M 39/0247;
(Continued)

(56) References Cited

U.S. PATENT DOCUMENTS 5,431,694 A * 7/1995 Snaper ..................... H02N 2/18
607/35
6,887,202 B2 * 5/2005 Currie .................. A61B 5/0059
600/309

(Continued)

FOREIGN PATENT DOCUMENTS

| JP | 2002543942 A | 12/2002 |
|----|--------------|---------|
| JP | 2008522769 A | 6/2006 |
| JP | 2009526567 A | 8/2007 |

OTHER PUBLICATIONS

PCT International Preliminary Report on Patentability for PCT Application No. PCT/US2013/076266 dated Jul. 2, 2015 (7 pages).
(Continued)

*Primary Examiner* — Bhisma Mehta
*Assistant Examiner* — Hamza Darb
(74) *Attorney, Agent, or Firm* — Blakely, Sokoloff, Taylor & Zafman LLP

(57) ABSTRACT

Various medical implants and methods of using the implants are disclosed. In an embodiment, the implants include piezoelectric polymers for treating unwanted medical conditions of a patient. The medical implants may be delivered to an organ of the patient to treat conditions of those organs.

22 Claims, 14 Drawing Sheets

(51) Int. Cl.
   *A61N 1/362* (2006.01)
   *A61F 7/12* (2006.01)
   *A61M 39/02* (2006.01)

(52) U.S. Cl.
   CPC ......... *A61N 1/3627* (2013.01); *A61N 1/3785* (2013.01); *A61F 2007/126* (2013.01); *A61M 2039/0258* (2013.01); *A61M 2039/0261* (2013.01)

(58) Field of Classification Search
   CPC .. A61M 2039/0261; A61M 2039/0258; A61M 25/0158; A61M 2025/0058; A61M 2205/0272; A61F 7/12; A61F 2007/126; A61K 9/0009; A61K 9/0097
   See application file for complete search history.

(56) References Cited

U.S. PATENT DOCUMENTS

| | | | |
|---|---|---|---|
| 7,410,497 B2* | 8/2008 | Hastings | A61B 5/0215 607/115 |
| 2009/0308742 A1* | 12/2009 | Paranjape | A61B 5/0537 204/403.1 |
| 2010/0292632 A1 | 11/2010 | Mulvihill et al. | |

OTHER PUBLICATIONS

PCT International Search Report and Written Opinion for PCT International Appln No. PCT/US2013/076266 filed on Dec. 18, 2013 (8 pages).

* cited by examiner

B-B

C-C

PIEZOELECTRIC MEDICAL IMPLANT

This application is a U.S. National Phase Application under 35 U.S.C. §371 of International Application No. PCT/US2013/076266, filed Dec. 18, 2013, which claims the benefit of U.S. Provisional Patent Application No. 61/738,517 filed Dec. 18, 2012, and this application hereby incorporates herein by reference these previous patent applications.

BACKGROUND

The present invention relates to electrical stimulation and thermal therapies for various medical conditions. More particularly, embodiments of the present invention relate to medical implants that include piezoelectric materials and/or heating elements, and methods of using the implants to treat unwanted conditions in a patient.

Coronary Heart Disease is the leading cause of death in the Western world making it an important public health concern. Acute Myocardial Infarction (AMI) events play a key role in Coronary Heart Disease. In addition to being potentially lethal, AMI may lead to the development of congestive heart failure (CHF), a leading cause of hospitalization after AMI. The cornerstone of AMI management aims for myocardial salvage and prevention of complications caused by the event. Medical efforts are focused on increasing the supply of oxygen to the myocardium through primary angioplasty, thrombolytic therapeutics, and coronary vasodilation (nitroglycerin), and at the same time reducing ischemic myocardium oxygen consumption via β-blockers and angiotensin-converting enzyme (ACE) inhibitors. Ancillary therapeutics or anticoagulants such as non-fractionated heparin, low molecular weight heparin, or lipid lowering statins may also be administered to reduce the recurrence of ischemic events. Despite the existence of these therapies, additional therapies to manage the impacts of AMI are needed.

Electrical stimulation may be used as a pro-healing trigger after an AMI event. One potential target for electrical stimulation is angiogenesis. As angiogenesis takes place in tissue, the surrounding endothelial cells are exposed to an electric field due to the active ion transport across the epithelia. Research has attempted to control angiogenesis using electric fields and has succeeded in showing that electrical stimulation induces significant angiogenesis in vivo, possibly as a result of an observed increase in vascular endothelial growth factor (VEGF) in muscle cells. Thus, studies suggest that electric field generation could play a positive role in post-infarct healing by inducing or supporting angiogenesis.

In addition to electrical stimulation, thermal stimulation has been shown to induce healing in cardiac cells and tissue in the form of revascularization and angiogenesis. In infarcted myocardium, necrotic tissue is gradually replaced by scar tissue, which often leads to further diastolic dysfunction resulting from the limited contractile properties of scar tissue. Additionally, post-infarcted myocardium sees cardiomyocytes replaced by myofibroblasts, which do not have the functionality necessary for cardiac contraction. However, thermal stimulation of infarcted myocardium may positively affect the myocardial healing process and aid in regaining cardiac function. Thermal stimulation of cardiac tissue may induce heat shock protein (HSP) expression, which provides cardiac protection and maintains tissue viability. Thermal stimulation has also been shown to impact cell migration, which is essential in replacing ischemic tissue with new functional tissue. Such replacement involves cell replication that occurs until the injured area is covered with cells. Therefore, thermal stimulation can cause cell migration, potentially encouraging endothelial cells to repopulate the site of injury and triggering cardiomyocyte reorganization.

Thermal stimulation can also induce growth factor production and capillary growth. The application of heat causes vasodilation to occur and increases the permeability of the vascular wall. This mechanism increases the antioxidative enzyme, catalase, which aids in reperfusion recovery. Thus, thermal stimulation can lead to cell differentiation and capillary growth by triggering growth factor production.

Like Coronary Heart Disease, diabetes is another medical condition with a high global incidence. Glucagon-like-peptide-1 (GLP-1) is a hormone derived from the transcription product of the pro-glucagon gene. GLP-1 has been shown to play a central role in glucose tolerance and has thus raised questions about its possible involvement in the pathogenesis of diabetes. The major source of GLP-1 in the body is the intestinal L cell that secrete GLP-1 as a gut hormone. The infusion of native GLP-1 using an insulin pump has been studied, but the use of native GLP-1 to treat diabetic patients is limited because the peptide cannot be taken orally and because it is rapidly metabolized in the circulatory system. Accordingly, methods of stimulating the production of GLP-1 in the gut may prove to be a useful therapy for diabetes. Recent evidence suggests that small intestinal electrical stimulation reduces food intake, although the mechanism of action is debated.

SUMMARY OF THE DESCRIPTION

Medical implants and methods of using the implants are disclosed. In an embodiment, a medical implant having a piezoelectric patch with a flexure area is provided. The flexure area may be sized to include a width, a length 1 to 20 times the width, and a thickness 0.01 to 0.15 times the width. In an embodiment, the flexure area includes a piezoelectric polymer and is configured to undergo mechanical strain caused by a target anatomy. For example, the target anatomy may cause bending in the flexure area. In an embodiment, the piezoelectric polymer may include a poled polymer, such as poled poly(vinylidene difluoride) (PVDF).

The medical implant may include an anchor to secure the flexure area to the target anatomy. The anchor may have various configurations. For example, the anchor may include one or more barbs to secure the flexure area to the target anatomy. In an embodiment, the anchor includes an adhesive to secure the flexure area to the target anatomy.

The medical implant may include a heating element coupled with the piezoelectric patch. The heating element may be at least partially within the piezoelectric patch and/or a portion of the heating element may be outside of the piezoelectric patch. In an embodiment, the heating element includes a metal susceptible to heating induced by magnetic resonance imaging (MRI). The heating element may have various configurations. For example, the heating element may include a coiled wire and/or a serpentine wire.

The medical implant may include a drug delivery mechanism. For example, the drug delivery mechanism may include a drug depot in the flexure area. The drug depot may be filled with a drug. In an embodiment, the drug-filled depot is covered by a membrane.

In an embodiment, a method of treating a patient tissue includes delivering a medical implant having a piezoelectric patch including a flexure area and an anchor to a target anatomy. The method may further include securing the flexure area to the target anatomy. The flexure area may include a poled PVDF polymer and the medical implant may also include a heating element coupled with the piezoelectric patch. The flexure area may be configured to undergo mechanical strain caused by the target anatomy. Voltage generated within the flexure area, e.g., in response to the mechanical strain, may be directed to the target anatomy. Heating generated in the heating element, e.g., by external stimulation from an external source, may be directed to the target anatomy. In an embodiment, the medical implant may include a drug delivery mechanism to deliver a drug to the target anatomy. Thus, the method may include electrical, thermal, and drug therapy of the target anatomy. For example, the target anatomy may be an intracorporeal site of a patient, such as a site that includes muscle tissue undergoing cyclic motion, e.g. cardiac muscle. Additionally, the target anatomy may move peristaltically, such as ilial site in small intestine generating peristaltic motion generates local electric voltage in the flexure area.

DETAILED DESCRIPTION

Figure 1:
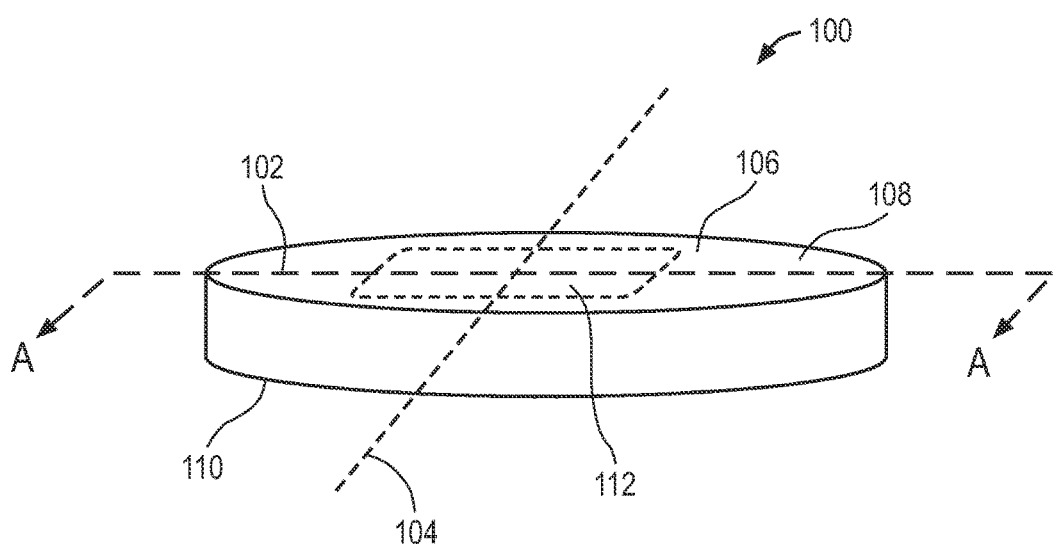
FIG. 1 is a perspective view illustration of a medical implant in accordance with an embodiment of the invention.

In various embodiments, description is made with reference to the figures. However, certain embodiments may be practiced without one or more of these specific details, or in combination with other known methods and configurations. In the following description, numerous specific details are set forth, such as specific configurations, dimensions and processes, etc., in order to provide a thorough understanding of the present invention. In other instances, well-known processes and manufacturing techniques have not been described in particular detail in order to not unnecessarily obscure the present invention. Reference throughout this specification to "one embodiment," "an embodiment", or the like, means that a particular feature, structure, configuration, or characteristic described in connection with the embodiment is included in at least one embodiment of the invention. Thus, the appearances of the phrase "one embodiment," "an embodiment", or the like, in various places throughout this specification are not necessarily referring to the same embodiment of the invention. Furthermore, the particular features, structures, configurations, or characteristics may be combined in any suitable manner in one or more embodiments.

The following description of several embodiments describes non-limiting examples that further illustrate the invention. No titles of sections contained herein, including those appearing above, are limitations on the invention, but rather they are provided to structure the illustrative description of the invention that is provided by the specification. The singular forms "a", "an", and "the" include plural referents unless the context clearly indicates otherwise. Any mention of an element includes that element's equivalents as known to those skilled in the art. Any methods and materials similar or equivalent to those described in this document can be used in the practice or testing of the present invention. This disclosure incorporates by reference all publications mentioned in this disclosure and all of the information disclosed in the publications. The features, aspects, and advantages of the invention will become more apparent from the following detailed description, appended claims, and accompanying drawings.

In the following description, various terms are used, and several of these terms are defined here at the outset. The following definitions, however, are not intended to be limiting of the invention described using these terms. The terms "subject," "individual," and "patient," used interchangeably in this disclosure, refer to any subject, generally a mammal (e.g., human, canine, feline, equine, bovine, rodent, etc.), in which delivery to or into an organ is desired. "Organ", "anatomy", "target organ", or "target anatomy" as used in this disclosure refers to any internal organ or anatomy to or into which site-specific activity is desired. The term "therapeutically effective amount" means a dosage of a drug, or a rate of delivery of a drug, that helps cause a therapeutic effect. As used in this disclosure, the terms "treatment", "treating", and the like, refer to obtaining a desired pharmacologic or physiologic effect. The effect may be prophylactic—completely or partially preventing a disease or symptom of a disease—or may be therapeutic—completely or partially curing a disease or adverse effect of the disease. "Treatment", as used in this disclosure, covers any treatment of a disease in a mammal, particularly in a human, and includes: (a) preventing the disease from occurring in a subject which may be predisposed to the disease but has not yet been diagnosed as having it; (b) inhibiting or slowing the disease's progress; or (c) relieving the disease. The terms "drug formulation", "formulation," and "drug," may be used interchangeably in this disclosure and encompass any substance suitable for delivery to a subject organ. The substances can include pharmaceutically active drugs, as well as biocompatible substances that do not by themselves exhibit a pharmaceutical activity, but that provide for a desired effect at a treatment site. Moreover, "Drugs" are intended to include, but are not limited to, drugs, biologically active agents, chemically active agents, therapeutic agents, and the like, and pharmaceutical compositions of these, which can be delivered to a treatment site. Drugs may contain a mixture of active agents. The term "condition", as used in this disclosure, refers to any abnormal or pathological condition, particularly one associated with an organ that a patch of the invention is useful for treating. Anything that should be treated falls under the definition of "condition".

In one aspect, embodiments of the invention describe a medical implant useful for delivering electrical energy into a target organ or into target tissue. The implant may be embodied in various configurations suited to a target anatomy. For example, in an embodiment, the implant comprises a piezoelectric material, such as a poled piezoelectric polymer. The piezoelectric material of the implant may generate electricity in response to strain applied to the implant, and the electricity may electrically stimulate the underlying tissue to provide, e.g., treatment of congestive heart failure or diabetes.

In another aspect, an embodiment of the invention includes a heating element connected with a medical implant useful for delivering thermal energy into a target organ or into target tissue. The heating element may be connected to an outer surface of the medical implant or at least partially embedded within the implant. In an embodiment, the heating element includes a metallic material tuned to heat when magnetic energy is supplied. For example, heat may be induced in the heating element by placing the implantable patch within the field of a magnetic resonance imaging (MRI) machine. The induced heat may thus be applied to the underlying tissue, e.g., to effect cell migration and replacement of ischemic tissue.

Referring to FIG. 1, a perspective view illustration of a medical implant 100 is shown in accordance with an embodiment of the invention. As seen if FIG. 1, a medical implant includes a substantially flat material in the shape of a piezoelectric patch 106. Piezoelectric patch 106 may have a substantially round configuration, an elliptical configuration, or any other shape that allows the patch to cover all or part of a target anatomy, such as an infarcted region of cardiac tissue.

In an embodiment, piezoelectric patch 106 may include a major axis 102 and a minor axis 104, defining an upper surface 108 of the patch in a two-dimensional space. For example, in the case of a circular or square upper surface 108, the ratio of the length along the major axis 102 relative to the length along the minor axis 104 may be about 1:1. However, in the case of an elliptical or rectangular upper surface 108, the ratio of the length along the major axis 102 relative to the length along the minor axis 104 may be from about 1:1.1 to 1:50.

Piezoelectric patch 106 need not take the shape of a conic section or a basic geometric shape. In some embodiments, the shape of piezoelectric patch 106 is selected to customize a fit of the patch to a target anatomy. For example, a longer, thinner organ such as a vasculature may have a matching longer, thinner piezoelectric patch 106. Similarly, piezoelectric patch 106 may have a contour that conforms with a surface of the target anatomy. For example, piezoelectric patch 106 may have a cylindrical contour to facilitate wrapping around a tubular target organ to one degree or another. As an alternative example, piezoelectric patch 106 may be pre-formed to conform with an apex of a left ventricle, or within or around another contoured tissue surface. In this regard, a geometry of piezoelectric patch 106 may be customized to a target tissue area. For example, in the case of an infarcted cardiac tissue, the infarcted area may be known through diagnostic procedures, and thus, piezoelectric patch 106 may be sized to fit over cover all or a majority of the infarcted area. For example, piezoelectric patch 106 may be sized to cover at least about 0.9 times the diagnosed infarct area and/or extend beyond the margins of the infarcted zone, covering an area of up to about 1.5 times the diagnosed infarct area.

In an embodiment, piezoelectric patch 106 may include a lower surface 110 opposite to upper surface 108, and thus, a thickness may be defined between upper surface 108 and lower surface 110. Thickness may be less than 10 percent of the length along major axis 102 or width along minor axis 104. In other embodiments, thickness may be less than 50 percent, 40 percent, 30 percent, or 20 percent of the length or width dimension.

In an embodiment, piezoelectric patch 106 includes a flexure area 112 that is sized and configured to undergo mechanical strain when piezoelectric patch 106 is applied to a target anatomy that moves. For example, flexure area 112 may bend when piezoelectric patch 106 is applied over a portion of a patient's heart, given that the heart relaxes during diastole and contracts during systole, and therefore, rhythmically applies motion to the flexure area 112. Flexure area 112 may include a piezoelectric material to generate electrical energy in response to this cyclical motion. Thus, flexure area 112 may have a size that covers a target area of a target anatomy and/or is sufficiently large to generate electrical energy in response to motion of the target area. More particularly, flexure area may be sized to provide sufficient electrical stimulation of the target anatomy in response to motion of the target area. In an embodiment, flexure area 112 may have a surface area of between about 1 square inch to 50 square inches. Accordingly, flexure area 112 may be large enough to cover and supply electrical stimulation to infarcted areas of a heart tissue. However, it will be appreciated that this range of sizes is exemplary, and may be changed to accommodate various infarct zones and/or other target anatomies. Placement of the patch may require optimal location in order to maximize effect on the target tissue, for example in the case of a cardiac patch, the hibernating myocites zone may be targeted in addition to the infarcted zone.

In various embodiments, flexure area 112 includes a material that acts as an effective piezoelectric material. Piezoelectric materials are materials that undergo a charge separation when the material is mechanically deformed. The charge separation causes an electric field in the region near the piezoelectric material. Even a slight deformation causes charge separation. In like manner, when an electric field is applied to a piezoelectric material, the material mechanically changes shape or deforms.

A variety of piezoelectric materials, including naturally occurring minerals, are available. In cases where the piezoelectric material is polymeric or co-polymeric, whether as a bulk material or as particles of a polymer combined with a binder, the polymer or copolymer can be any polymer or copolymer that exhibits piezoelectricity. For example, the piezoelectric polymer may be polyvinylpyrrolidone (PVP), poly(vinyl-pyrrolidone-fluoride-co-hexafluoro-propylene) (PVP-HFP), or poly(vinylidene difluoride) (PVDF), to name a few. In an embodiment, the piezoelectric material is inorganic or substantially inorganic. Any inorganic piezoelectric or substantially inorganic piezoelectric material that can meet the other material constraints of medical implant 100 may function as the piezoelectric material of this invention.

In some embodiments, the piezoelectric effect of the material is enhanced by partially aligning the charge-separation dipoles with each other. In cases where the binder (whether piezoelectric or not) or the bulk material itself are polymeric, the piezoelectric effect in some embodiments may be enhanced by creating a poled polymer piezoelectric. That is, the material may be treated to change the essentially random piezoelectric dipoles into dipoles that have a greater degree of alignment in one or more directions. Piezoelectric polymers treated using these or any other myriad of parameters are "poled polymers" if the treatment actually achieves an improvement in dipole alignment.

One way of creating a poled polymer is to stretch the polymer to create charge-separated dipoles and to apply an electrical or magnetic field to the polymer in the stretched state. Alternatively or additionally, a poled polymer can be heated during the application of the magnetic field or the electric field. The heating can occur before, during, or after stretching. Furthermore, the heating can occur before, during, or after electric or magnetic field application. Generally, the amount of heating is chosen to raise the temperature of the polymer enough that the polymer chains move across each other, but well below a temperature that would cause phase transitions, melting, or any other deleterious effect. One type of poled polymer is PVP film that has been stretched in its planar dimensions, heated, and then subjected to an electrical field. The stretching and the electrical field are maintained as the heat is removed and the polymer cools. This type of treatment can be carried out on PVP-HFP, as well.

PVDF exists in different crystal phases and can be manipulated by stretching, annealing, and poling procedures to convert from one crystal phase to another. The manipulation of the PVDF's crystal phase can render the material more piezoelectric. PVDF is typically a semi-crystalline material and its volume fraction of crystalline material may generally be between 50 percent to 60 percent depending on thermal history. Its composition is primarily spherulitic structures of lamellae, which grow outward from the center of the spherulite. It may have the common stacking faults, grain boundaries, and other course defects expected in a semi-crystalline solid. It may consist of long chain molecules with repeating units, and its simplicity allows for some stereochemical constraint to the main structure but also high flexibility. The piezoelectric coefficients of PVDF are dependent on parameters such as temperature and crystallinity but can also be enhanced by mechanical orientation, thermal annealing, and high voltage treatment. These can all induce a crystalline phase transformation by changing randomly oriented a crystalline structure of PVDF into the semi-crystalline 0 structure by stretching the film to a ratio of greater than 1:1. For example, the film may be stretched to a ratio of at least 2:1. For example, the film may be stretched to a ratio of 4:1 or greater. The stretching may also be applied within a specific temperature range so that there is sufficient molecular mobility for the polymer segments to realign themselves, without sliding past one another at an excessive temperature. For example, stretching may be applied at a temperature between about 60-130 degrees Celsius. More particularly, stretching may be applied at a temperature between about 90-110 degrees Celsius. In order to maximize the piezoelectric nature of PVDF, and therefore the potential for electrical stimulation, preliminary work was performed in our laboratory to explore the effects of stretching and poling on PVDF films.

Stretching of PVDF can be done in one or more directions. When stretching is applied along the single machine axis, it is referred to as uniaxially stretching, and when stretching is applied along the machine and transverse axes, it is referred to as bi-axially stretching. The uniaxial stretching of PVDF may result in a uniform thickness, isotropic properties, no wrinkling when heated, and long term stability.

Poled PVDF films demonstrate tensile, thickness, and shear piezoelectricity similar to piezoelectric ceramics. Poling is a process that does not reorient the grain boundaries, but rather reorients the domains within the individual grains in the direction of the applied field. Specifically, reorientation is caused by chain rotation about a C-C chain axis. In the absence of electric fields, dipoles are observed to align in a random fashion. These randomly aligned dipoles can be rearranged into a poled orientation by heating the films above a specific temperature while applying an electric field across the film. Poling may be performed under various electric field conditions. For example, poling may occur under an electric field of 65 MV/m. However, lesser electric fields, such as between about 5 kV to 2000 kV may also be used. In an embodiment, poling may be performed under an electric field between about 5 to 7 kV. Cooling the film without removing the electric field will freeze dipoles into the desired orientation.

In some embodiments, medical implant 100 may be configured to attach to the outside of a target anatomy, such as an organ or other patient tissue. For example, in an embodiment, at least one side of the patch has an adhesive for attaching piezoelectric patch 106 to an exterior wall of an organ or to an interior wall of an organ cavity. The adhesive may be selected from biostable or biodegradable adhesives depending upon the time that piezoelectric patch 106 is intended to remain inside the subject. Such adhesives may include, for example, bioadhesives such as adhesive proteins derived from various natural organisms. Furthermore, biomedical adhesives, such as polysaccharide-based adhesives may be used. One skilled in the art may contemplate the use of other adhesives formulated to provide temporary or permanent adhesion of medial implant 100 to a target anatomy. The toxicity of the adhesive may be selected to be low enough that any negative effect brought about by the adhesive's presence on piezoelectric patch 106 is substantially outweighed by the positive effects the patch has on the subject. An alternative to using an adhesive is to use structures such as hooks or barbs mounted in piezoelectric patch 106 and configured to penetrate the tissue that piezoelectric patch 106 mounts on.

Figure 2A:
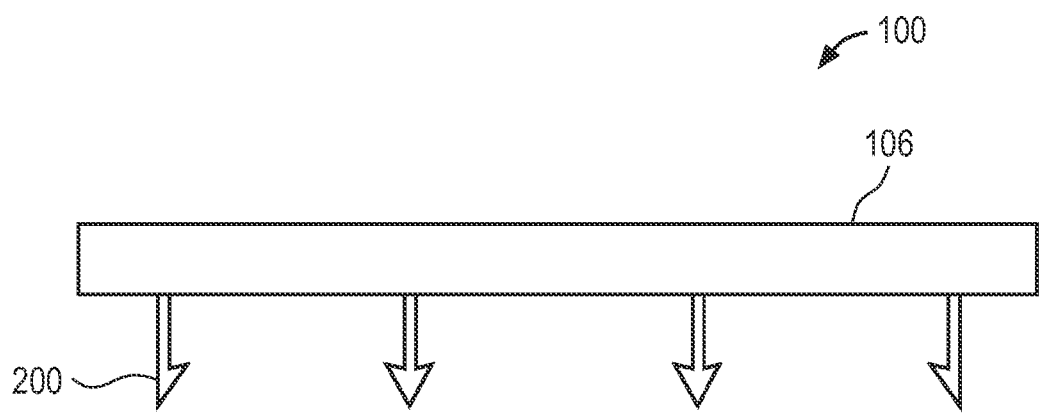
FIG. 2A is a cross-sectional view, taken about line A-A of FIG. 1, of a medical implant having a barb anchor in accordance with an embodiment of the invention.

Referring to FIG. 2A, a cross-sectional view, taken about line A-A of FIG. 1, of a medical implant having a barb anchor is shown in accordance with an embodiment of the invention. An anchor 200 may be monolithically formed with a portion of piezoelectric patch 106, or anchors 200 may be bonded or otherwise attached to piezoelectric patch 106. In an embodiment, anchor 200 includes one or more barbs that permit anchor 200 to puncture a target anatomy, e.g., muscle tissue, but to resist removal of piezoelectric patch 106 after the target anatomy has been engaged. Barb anchors 200 may vary structurally, but in an embodiment, a barb anchor 200 includes a shaft extending distally to a point capable of puncturing tissue. Furthermore, the anchor 200 may include one or more barbs directed opposite to the point, such that once the barb has followed the point into the puncture site, it resists removal by engaging tissue along the path of puncture.

Figure 2B:
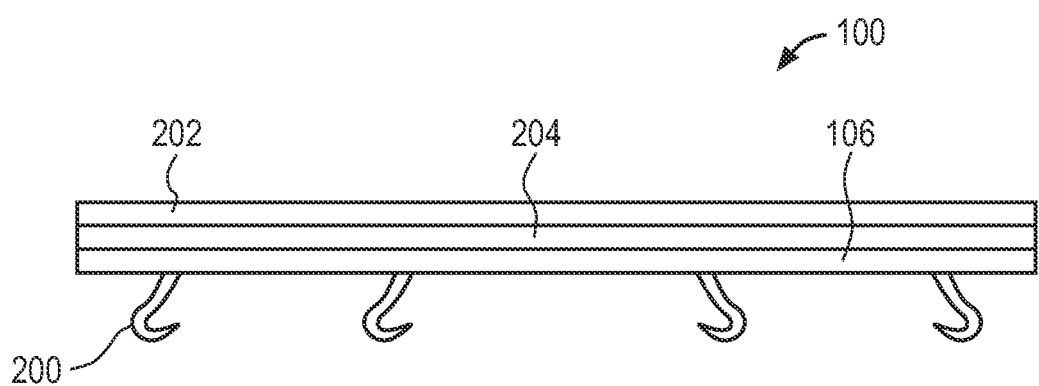
FIG. 2B is a cross-sectional view, taken about line A-A of FIG. 1, of a medical implant having a hook anchor in accordance with an embodiment of the invention.

Referring to FIG. 2B, a cross-sectional view, taken about line A-A of FIG. 1, of a hook anchor of a piezoelectric patch in accordance with an embodiment of the invention. In an embodiment, hook anchors 200 include hooks with points that can puncture and grip a target anatomy and/or tissue. Individual hook anchors 200 may have hooks pointing in various directions, such that when all hooks are engaged with the target anatomy, movement of piezoelectric patch 106 in any direction is resisted by at least one hook.

In an embodiment, rather than using adhesives or mechanical fasteners to attach piezoelectric patch 106, external elements may be utilized to secure medical implant 100 to an underlying tissue. For example, medical implant 100 may be delivered endoscopically or during an open-chest procedure, and sutures or staples that are commonly used in such procedures may be applied to fasten piezoelectric patch 106 to the target anatomy.

Still referring to FIG. 2B, in an embodiment, medical implant may be a composite structure having multiple structural components making up the patch body. For example, medical implant 100 may include a laminate structure formed from at least two adjacent layers. In an embodiment, medical implant 100 includes piezoelectric patch 106 facing toward a target anatomy and bonded with outer laminate 202 and/or inner laminate 204. The layers of medical implant 100 may be adhered with one another using an adhesive, or alternatively, may be mechanical fastened, e.g., using snap fits, or other mechanical retention features. In an embodiment, piezoelectric patch 106 generates electricity over a surface area facing a target tissue, but inner laminate 204 and outer laminate 202 are formed from non-piezoelectric materials that do not generate electricity. Non-piezoelectric portions of medical implant 100, such as inner laminate 204 and outer laminate 202, may instead be selected for other material properties, such as flexibility, strength, insulation, etc. Numerous non-piezoelectric materials may be used, such as various polyimide, polyamide, polyurethane, polyether block amide, nylon, etc. formulations. Furthermore, biodegradable non-piezoelectric polymers may be used, such as various poly (L-lactide), poly (D-lactide), poly (DL-lactide), polycaprolactone, etc. formulations. One skilled in the art may contemplate other useful non-piezoelectric materials, and thus, this listing is not intended to be exhaustive.

In an embodiment, the structural components of medical implant 100, e.g., piezoelectric patch 106 portion and/or laminate portions, are configured to be delivered to a target anatomy within a patient. For example, medical implant 100 may be delivered via percutaneous, subxiphoid, endoscopic, thoracoscopic, or laparoscopic delivery systems to target anatomies as diverse as the pericardium of the heart, the ileum of the small intestine, and any other anatomy. Thus, piezoelectric patch 106 and/or medical implant 100 may be constructed from materials that are flexible enough to fit into lumens, cavities, and puncture sites used for such delivery modalities.

Figure 3:
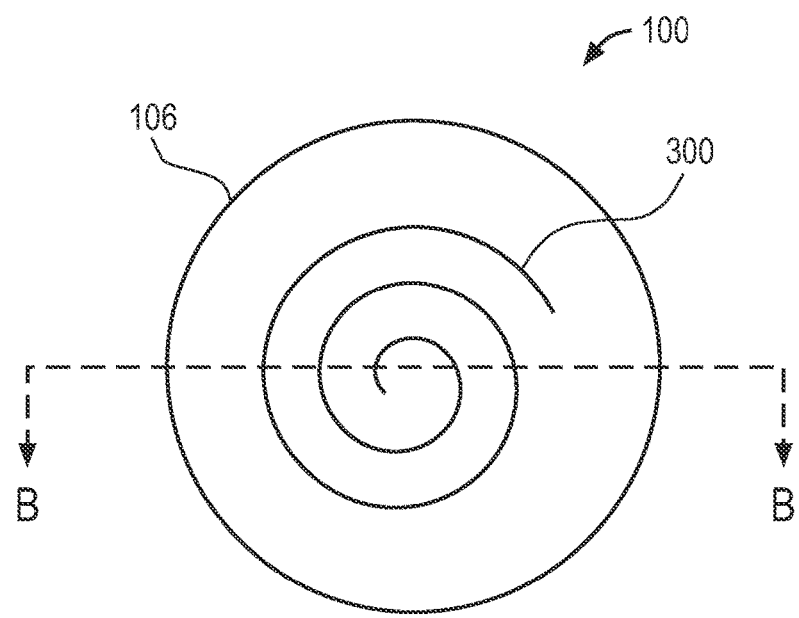
FIG. 3 is a top view of a medical implant having a coiled heating element in accordance with an embodiment of the invention.

Referring to FIG. 3, a top view of a medical implant having a coiled heating element is shown in accordance with an embodiment of the invention. In some embodiments, piezoelectric patch 106 includes a heating element 300 that generates heat to be transferred to the target tissue. There are several different methods to generate local heating in the cardiac region. One of the most promising prospects is utilizing the heat induced by MRI scans to locally heat tissue or an implant that would heat surrounding tissue. MRI heating is capable of controlling local temperatures within degrees, making it an ideal candidate for inducing heat. MRI systems reconstruct images from radiofrequency (RF) signals, which result in heating by scattering of the RF electrical field. A tissue specific absorption rate (SAR) of the electrical component of the time-variant radio frequency field, for example 128 MHz or 64 MHz corresponding to 3 T and 1.5 T magnetic field respectively, is enhanced in the presence of an electrically conductive implant. MRI time-varying RF field generated heating effect has been previously described. See IEEE Transactions on Device and Materials Reliability, Vol. 5, No. 3, September 2005, 467, "MRI and Implanted Medical Devices: Basic Interactions With an Emphasis on Heating", John A. Nyenhuis, *Senior Member, IEEE*, Sung-Min Park, Rungkiet Kamondetdacha, Arslan Amjad, Frank G. Shellock, and Ali R. Rezaifield.

The heating is most prevalent at the surface of the tissue and decreases as it gets deeper towards the center of the body. RF signals are perpendicular to the static field, also a product of MRI scans, and the RF signal is translated to heat in tissue depending on the qualities of the magnetic field. This heating approach has been successfully implemented in the past. Heating element 300 may become a target for MRI magnetic fields to induce heating in heating element 300 material. The oscillating magnetic field from an MRI may be applied through a patient to heating element 300 to induce an electrical field in the heating element 300. Induction of an electrical field occurs in accordance with antenna principles. Thus, heating element 300 may be shaped to facilitate this antenna-like electrical field induction. More specifically, heating element 300 may be a wire-like structure or a structure that forms a resonance loop. The width of the structure may be substantially less than the wavelength of the incoming magnetic field. For example, heating element 300 wires may be on the order of between about 0.5 to 3 mm in diameter, width, or thickness to facilitate electrical field induction. Furthermore, heating element 300 wires may have a total length of between about 5 to 40 cm to facilitate heating according to the frequency of the RF field. Alternatively, electrical field induction can also heat the heating element directly. Heating element 300 may have an electrical conductivity property to absorb and thermally conduct any electrical field generated by an external device with a frequency that produces inductive heating in the conducting implant. Thus, heat may be generated in the heating element 300 by external stimulation supplied from an external source. Heating element 300 may be copper, aluminum, and/or stainless steel although other materials may also be useful. The oscillating electrical field induced by an external source may encounter resistance in heating element 300, leading to heat generation. Thus, heat may be generated in response to the oscillating magnetic field. Heating element 300 may include any of a variety of forms. For example, heating element 300 may be coiled within a plane as shown in FIG. 3, such that the element radiates from the center of piezoelectric patch 106 toward an outer edge of piezoelectric patch 106. Alternatively, heating element 300 may be formed in other shapes, as described below, and may be shaped within a single plane, e.g., fully embedded within, or located outside of, piezoelectric patch 106—or be formed out of plane, e.g., partially embedded within piezoelectric patch 106 and partially formed over an outer surface of piezoelectric patch 106.

Heating element 300 may be formed from numerous materials that are able to convert electrical fields into internal heating of the element. For example, heating element 300 may be formed from metals, such as cobalt-chromium alloys, stainless steel alloys, nickel-titanium alloys, copper alloys, iron and/or ferrous alloys, nichrome, kanthal, or cupronickel. Alternatively, heating element 300 may be formed from a ceramic, such as molybdenum disilicide. Heating element 300 may be formed to have a circular or non-circular cross-section. For example, heating element 300 may be wire, e.g., round or tubular wire, or it may be foil, e.g., substantially rectangular. In some embodiments, the wire has a composition chosen to be substantially inert to a target anatomy and/or tissue.

Figure 4:
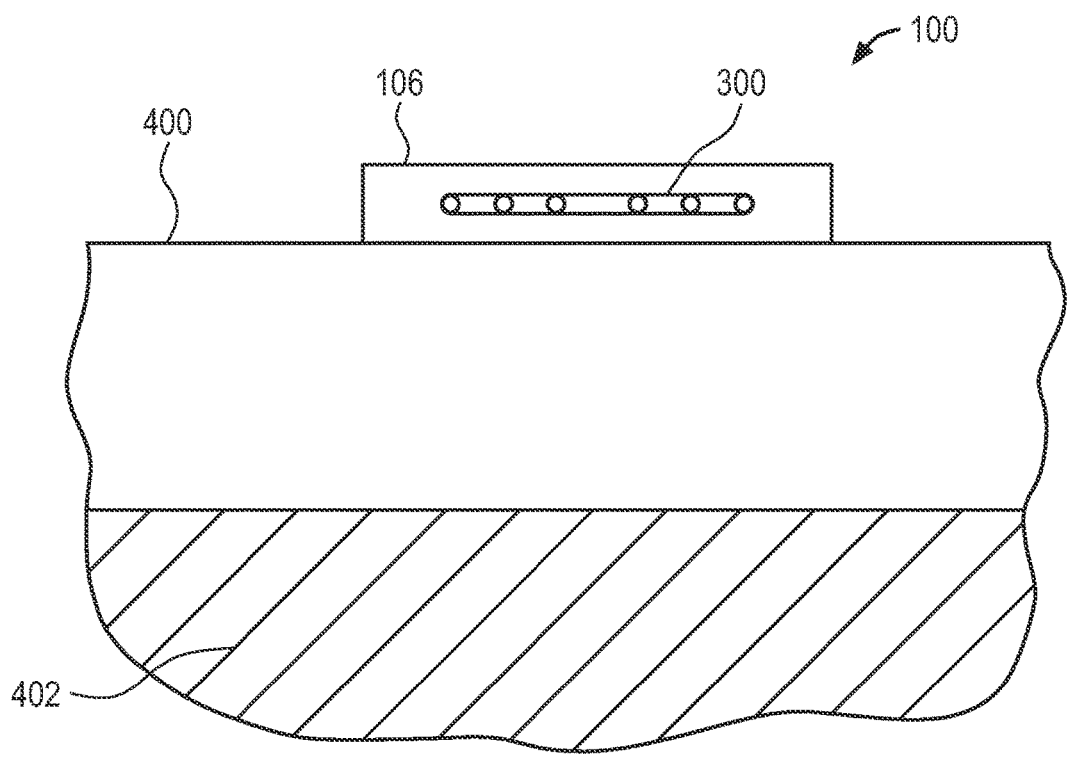
FIG. 4 is a cross-sectional view, taken about section line B-B of FIG. 3, of a medical implant placed on a pericardium in accordance with an embodiment of the invention.

Referring to FIG. 4, a cross-sectional view, taken about line B-B of FIG. 3, of a medical implant placed on a pericardium in accordance with an embodiment of the invention. In operation, piezoelectric patch 106 may be delivered to a heart of a patient in need of treatment. Piezoelectric patch 106 may be positioned external to the myocardium 402 and attached to the epicardium or pericardium 400 as shown in FIG. 4. Piezoelectric patch 106 may be positioned within the pericardial sac. Alternatively, piezoelectric patch 106 may be positioned within the myocardium 402 through a puncture of the epicardium or endocardium. Further still, piezoelectric patch 106 may be positioned within the cardiac cavities such as the right and/or left atrial appendages, within the cordae tendonae of the right and left ventricle 800, or attached to the interatrial septum. Piezoelectric patch 106 may further be attached to or incorporated into another cardiac implant, such as a mitral or aortic valve implant, or a coronary stent. Thus, piezoelectric patch 106 may be delivered in numerous manners to many areas of the heart 900. In any of these cases, piezoelectric patch 106 may be attached to heart 900 tissue using any of the anchor 200 features described above.

Once positioned on a target anatomy, piezoelectric patch 106 may move and flex as the target anatomy functions. For example, as the heart beats, pericardium 400, which follows the movement of the convulsing myocardium 402, will flex. Piezoelectric patch 106 placed over pericardium 400 may be flexible enough to minor the motion of the pericardium 400, i.e., to flex with the beating of the heart. Furthermore, as piezoelectric patch 106 repeatedly flexes in response to movement of the beating heart, the piezoelectric material within piezoelectric patch 106 generates an electrical field in the surrounding tissue.

As described above, in some embodiments, an external MRI device applies an alternating magnetic field to the implanted piezoelectric patch 106. Alternatively, the external, magnetic-field-supplying device may not be an MRI device, but may instead be a machine that generates a pulsed magnetic field without a large superconducting magnetic solenoid. Such a solenoid, which is required in an MRI to provide a uniform magnetic field gradient, may not be necessary to providing sufficient magnetic energy to induce heating in heating element 300. Furthermore, the magnetic-field-supplying machine may not require a delicate antenna to receive a signal, as is required in an MRI device. In either case, the applied magnetic field may induce heating of heating element 300 and that heat may be transferred to pericardium 400.

Figure 5:
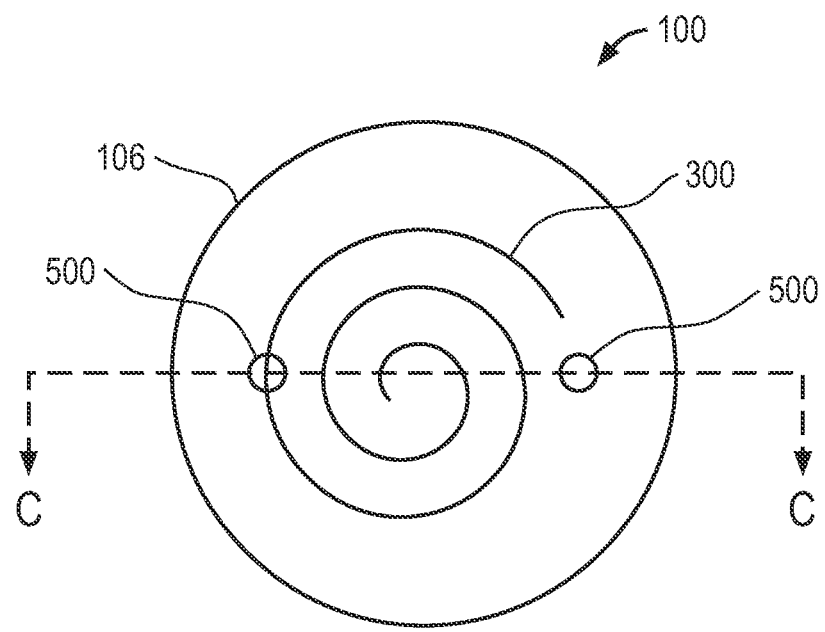
FIG. 5 is a top view of a medical implant having a coiled heating element and a drug pump in accordance with an embodiment of the invention.

Referring to FIG. 5, a top view of a medical implant having a coiled heating element and a drug pump is shown in accordance with an embodiment of the invention. In an embodiment, drug pump comprises one or more drug depots 500. Drug depot 500 may include a recess or reservoir formed in a surface of piezoelectric patch 106. For example, drug depot 500 may be a cylindrical recess formed into an upper or lower surface 110 of piezoelectric patch 106. Drug depot 500 may be formed using known manufacturing methods, such as mechanical machining, laser ablation, etc. Drug depot 500 may be filled with a drug and/or polymer. Drug depot 500 may contain any drug deemed suitable by one of ordinary skill in the art for a given application. For example, the drug may include anti-tumor necrosis factor antibody, anti-inflammatory (dexamethasone, clobetasol), metalloproteinase inhibitors, inhibitors of apoptosis, proangiogenic agents (VEGF, FGF), carioprotectives (IGF, adenosine, statins), or vasodilators (adenosine, nitroprusside) drugs. A more extensive listing of suitable drugs is provided below and may be referenced to select an appropriate drug for a target anatomy and/or therapeutic effect.

In an embodiment, piezoelectric patch 106 may include a membrane covering at least one drug depot 500. The membrane may impede movement of the drug and/or polymer from the drug depot 500. The membrane may control movement of the drug and/or polymer mechanically or chemically. For example, the permeability of the membrane to a drug within drug depot 500 may depend on a size of one or more pores or holes formed in the membrane through which the drug passes. Furthermore, the membrane may include a hydrophobic polymer or it may include a hydrogel or hydrophilic polymer. These polymers may provide varying resistance to drug mass transport, based on the physicochemical property of the drug and membrane material. The material of the membrane in combination with mechanical gates, e.g., holes and pores, may affect the delivery of drug from drug depot 500. In other embodiments, the membrane may be bioabsorbable, and thus, may prevent drug delivery until membrane has either partially or entirely degraded, at which time drug may be delivered from drug depot 500 to a target anatomy. Examples of suitable bioabsorbable materials for forming the membrane include various poly (L-lactic acid), poly (D-lactic acid), poly (DL-lactic acid), Poly (lactic-co-glycolic acid) polycaprolactone, etc. formulations.

In an embodiment, drug depot 500 allows for piezoelectric patch 106 to deliver a drug in a therapeutically effective amount. For example, the flexing of the heart during a heart beat may cause drug to be forced out of drug depot 500 toward the surrounding tissue. Drug may be squeezed directly from drug depot 500 in response to flexing of the piezoelectric patch 106. For example, as piezoelectric patch 106 follows the beating heart tissue, the edges of drug depot 500 may move toward each other, reducing the depot volume and forcing drug out of drug depot 500, either directly or through a membrane.

In an embodiment, the drug pumping action of piezoelectric patch 106 may be aided and/or driven by piezoelectrically induced mechanical motion of piezoelectric patch 106. For example, in addition to mechanical flexure of piezoelectric patch 106 caused by the beating heart, an external field applied to piezoelectric patch 106 may cause the piezoelectric material of piezoelectric patch 106 to change shape or flex, thereby supplying mechanical force to operate drug pump and control the delivery of the drug. Thus, medical implant 100 may act as a drug delivery device causing drug delivery to a target anatomy and providing a drug therapy to the target anatomy in addition to the electrical stimulation and/or thermal therapy provided by the piezoelectric patch 106.

Figure 6A:
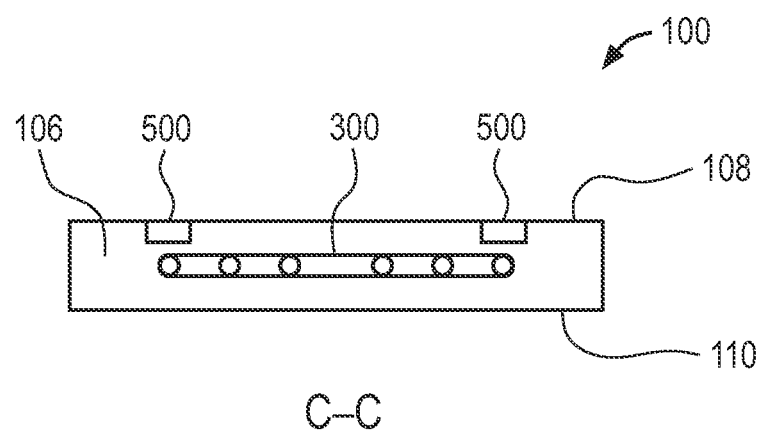
FIGS. 6A-6C are cross-sectional views, taken about line C-C of FIG. 5, of various embodiments of a medical implant having a coiled heating element and a drug pump in accordance with an embodiment of the invention.

Referring to FIG. 6A, a cross-sectional view, taken about section line C-C of FIG. 5, of an embodiment of a medical implant having a coiled heating element and a drug pump in accordance with an embodiment of the invention. In an embodiment, heating element 300 may be fully embedded within piezoelectric patch 106. As shown, heating element 300 may be approximately centered between an upper surface 108 and lower surface 110 of piezoelectric patch 106. Alternatively, heating element 300 may be off center. For example, heating element 300 may be embedded just above the lower surface 110. In an embodiment, the heating element 300 wire surface coincides with the lower surface 110. As shown, one or more drug depots 500 may be formed in piezoelectric patch 106 and filled with a therapeutic drug. Drug depots 500 may be directed toward or away from lower surface 110.

Figure 6B:
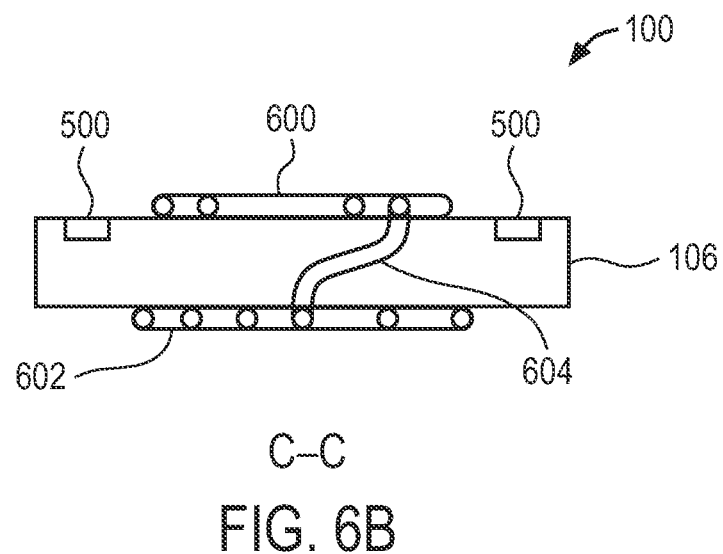

Referring to FIG. 6B, a cross-sectional view, taken about section line C-C of FIG. 5, of an embodiment of a medical implant having a coiled heating element and a drug pump in accordance with an embodiment of the invention. In an embodiment, heating element 300 may be partially embedded and partially exposed from piezoelectric patch 106. For example, heating element 300 may include an upper coil 600 formed over a top surface of piezoelectric patch 106 and a lower coil 602 formed over a bottom surface of piezoelectric patch 106. Upper coil 600 and lower coil 602 may therefore be separated by a thickness of piezoelectric patch 106. However, despite this physical separation, upper coil 600 and lower coil 602 may be thermally coupled by a thermal bridge 604 that is embedded within piezoelectric patch 106. Thermal bridge 604 may traverse the thickness of piezoelectric patch 106 to transfer heat generated in upper coil 600 to lower coil 602, and vice versa. For example, in a case where upper coil 600 is nearer to an MRI machine, and in which the material making up piezoelectric patch 106 is substantially insulating, a magnetic field directed at piezoelectric patch 106 may induce more heat in upper coil 600 than lower coil 602. Nonetheless, heat may be distributed evenly throughout thermal element via thermal bridge 604, to allow heat to be directed to tissue that lower coil 602 is positioned against. As in any of the described embodiments, piezoelectric patch 106 may include one or more drug depot 500 to effect drug therapy.

Figure 6C:
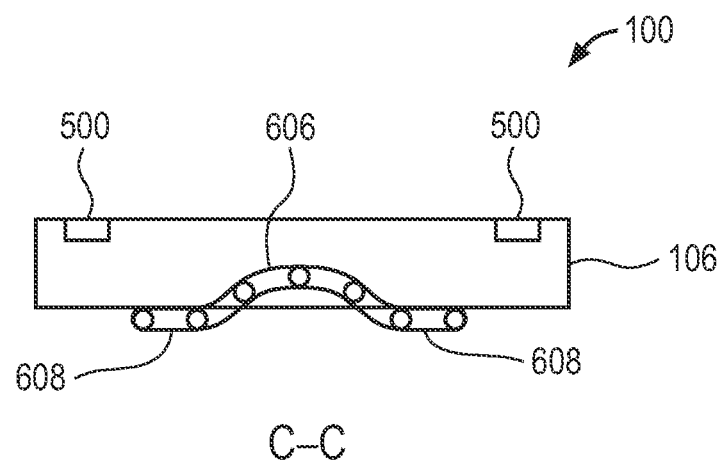

Referring to FIG. 6C, a cross-sectional view, taken about section line C-C of FIG. 5, of an embodiment of a medical implant having a coiled heating element and a drug pump in accordance with an embodiment of the invention. In an embodiment, heating element 300 may include an embedded portion 606 and an exposed portion 608. For example, heating element 300 may be a disc-shaped coil of wire or film having a convex contour. In an embodiment, an apex of the convex contour may be embedded within piezoelectric patch 106, forming embedded portion 606. In contrast, outer edges of the convex contour may be exposed outside of piezoelectric patch 106, forming exposed portion 608. Exposed portion 608 may be flattened against an outer surface of piezoelectric patch 106 and/or adhered to piezoelectric patch 106. For example, exposed portion 608 may be adhesively or thermally bonded to a surface of piezoelectric patch 106. As in any of the described embodiments, piezoelectric patch 106 may include one or more drug depot 500 to effect drug therapy.

Figure 7A:
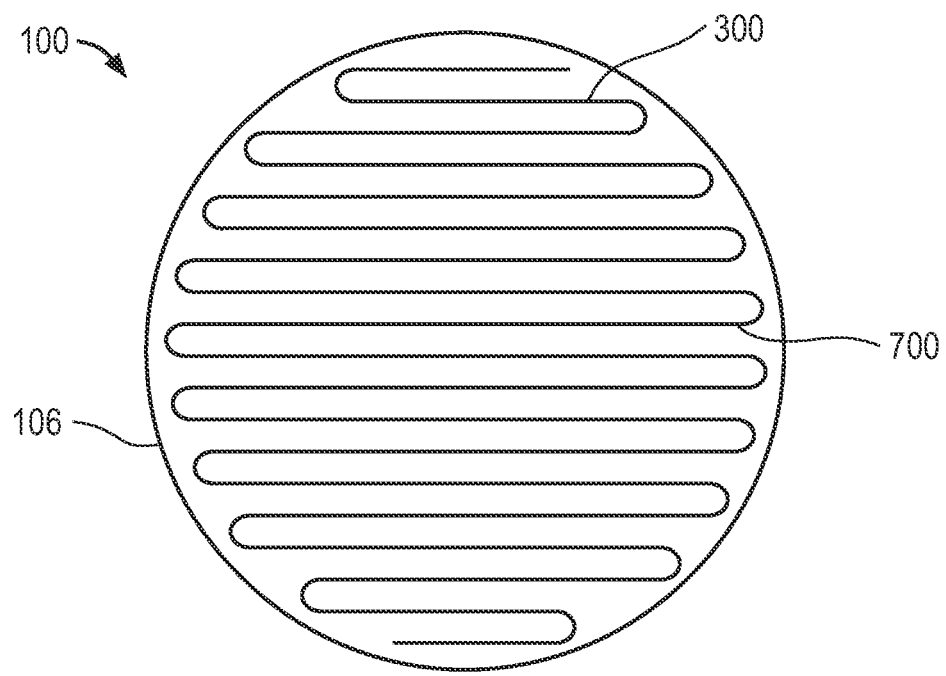
FIGS. 7A-7B are top views of a medical implant having various embodiments of a heating element in accordance with an embodiment of the invention.

FIG. 7A shows a top view of a medical implant having a heating element in accordance with an embodiment of the invention. In an embodiment, heating element 300 may include a serpentine shape, formed for example, by a serpentine wire 700. Serpentine as used here is intended to refer to any curvilinear shape that undulates, zig-zags, follows a sinusoidal path, etc. In addition, although serpentine wire 700 may include a wire with a circular cross-section, it is envisioned that a serpentine shape may also be formed from a foil, non-circular cross-section wire, tubular wire, etc. As described above, heating element 300 may be fully embedded, partially embedded, or as shown, fully exposed relative to piezoelectric patch 106. Therefore, heating element 300 may be retained by piezoelectric patch 106 by being integrated therein, e.g., embedded therein, or heating element 300 may be adhesively or thermally bonded to a surface of piezoelectric patch 106.

Figure 7B:
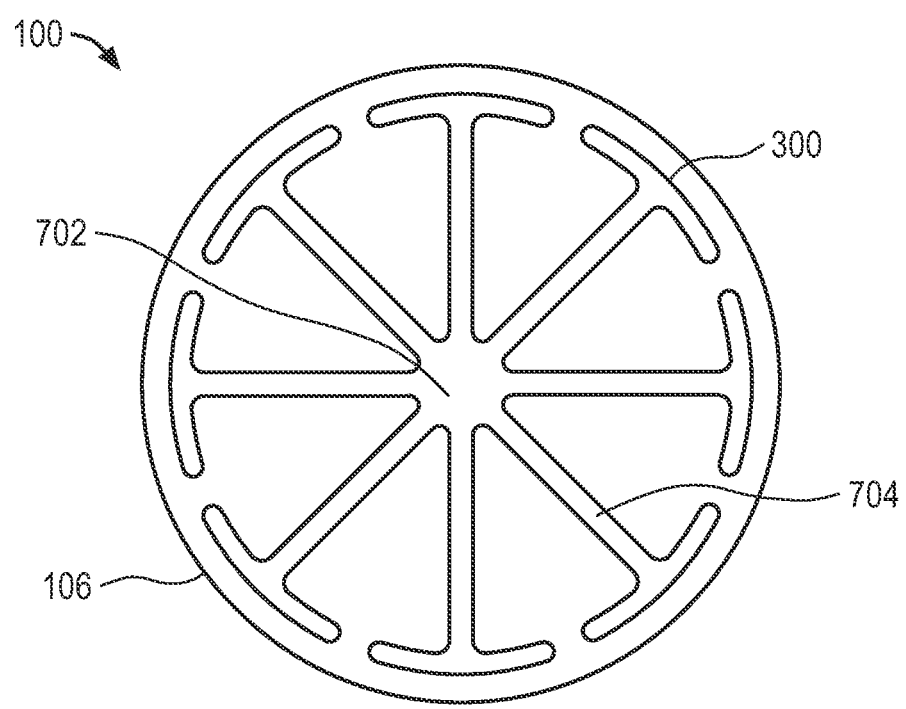

FIG. 7B shows a top view of a medical implant having a heating element in accordance with an embodiment of the invention. In an embodiment, heating element 300 may include a wheel shape, including a hub 702 portion and a spoke 704 portion. For example, heating element 300 may be include a foil or film that is formed in the shape of a wheel or another two-dimensional or three-dimensional shape having favorable flexibility. In an embodiment, spokes 704 may be sufficiently thin as to allow the outer edges of piezoelectric patch 106 to flex in accordance with the movement of a target anatomy. For example, spokes 704 may have a width dimension of about 0.030-inch and a thickness of about 0.003-inch. As described above, heating element 300 may be fully embedded, partially embedded, or as shown, fully exposed relative to piezoelectric patch 106. Therefore, heating element 300 may be retained by piezoelectric patch 106 by being integrated therein, e.g., embedded therein, or heating element 300 may be adhesively or thermally bonded to a surface of piezoelectric patch 106.

In addition to bonding metal wire or films to medical implant 100, heating element 300 may also be formed using known circuit printing techniques. For example, a metal film, e.g., copper, may be laminated on piezoelectric patch 106, piezoelectric strip, or any other medical implant 100 configuration. A portion of copper may then be removed using, e.g., etching, to leave a heating element 300 shape over the piezoelectric substrate. The heating element 300 shape may be patterned in any manner, such as in the coil or serpentine shapes noted above. Such circuit printing methods may provide adhesion between heating element 300 and the underlying substrate of medical implant 100 in a high-volume and economical process.

Figure 8A:
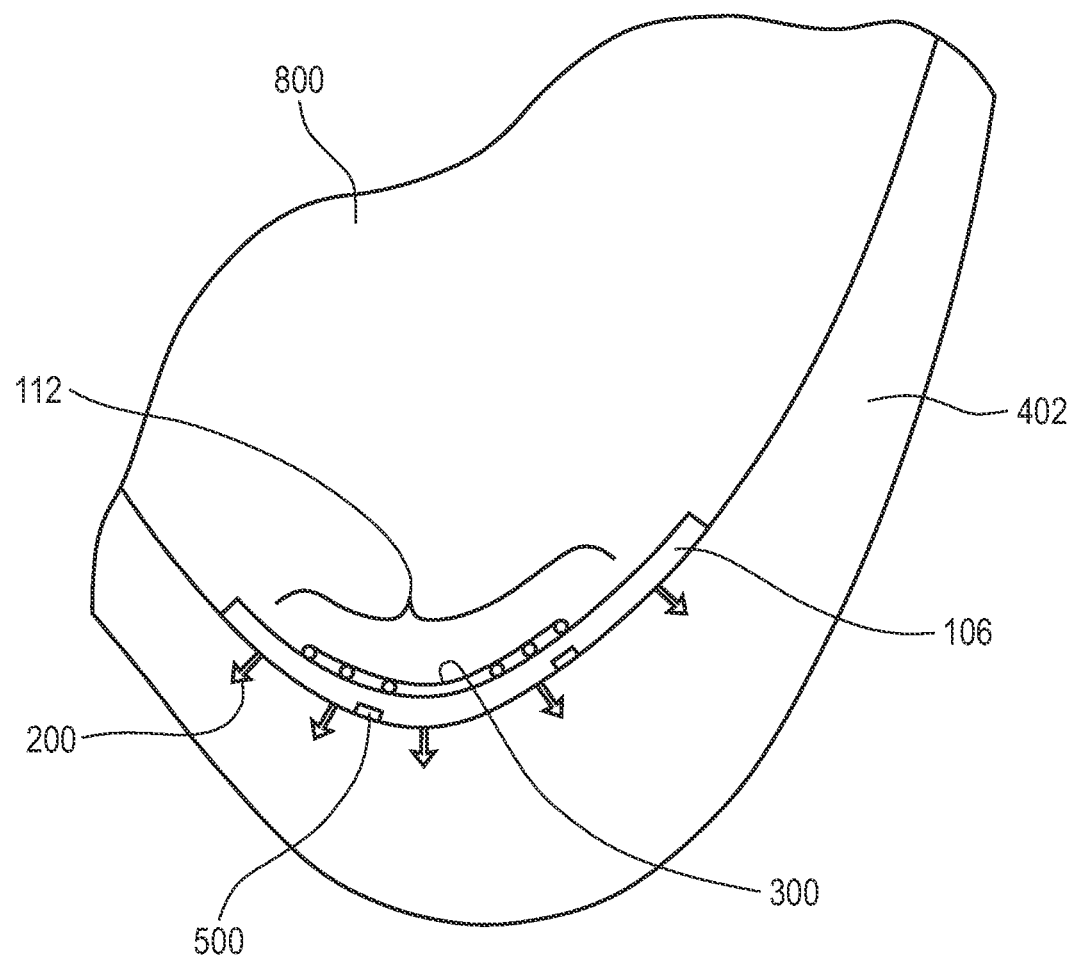
FIGS. 8A-8B are cross-sectional views of a medical implant placed in a left ventricle in accordance with an embodiment of the invention.

Referring to FIG. 8A, a cross-sectional view of a medical implant placed in a left ventricle is shown in accordance with an embodiment of the invention. As described above, anchoring features associated with piezoelectric patch 106 permit implantation on various target anatomies. For example, piezoelectric patch 106 may be placed on the pericardium 400, i.e., the sac surrounding the heart, or over the myocardium 402 beneath the pericardium 400. Alternatively, piezoelectric patch 106 may be implanted on an inner surface of the left ventricle 800. For example, piezoelectric patch 106 may be pressed against myocardium 402 of the left ventricle 800 near a lower apex of the ventricle. One or more anchor 200 may engage myocardium 402 and retain piezoelectric patch 106 by resisting removal. In an embodiment, piezoelectric patch 106 may include a heating element 300, for example, on a surface opposite from anchor 200, as well as one or more drug depot 500 located in the areas between anchor 200 and facing toward myocardium 402.

Figure 8B:
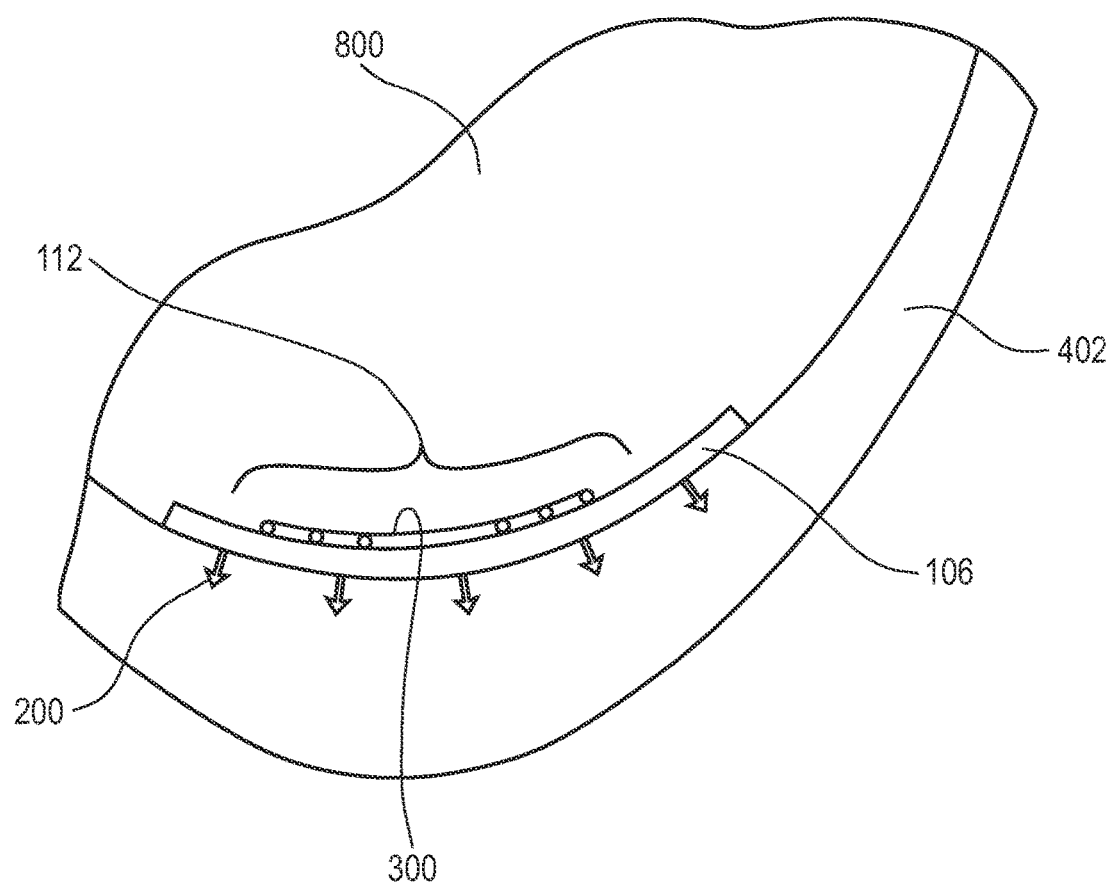

Referring to FIG. 8B, a cross-sectional view of a medical implant placed in a left ventricle is shown in accordance with an embodiment of the invention. In an embodiment, piezoelectric patch 106 includes flexure area 112 that traverses a distance such that as left ventricle 800 contracts and relaxes to pump blood, flexure area 112 flexes. For example, as shown in FIG. 8A, flexure area 112 has a radius of curvature matching the radius of the left ventricle 800 apex during diastole. Referring again to FIG. 8B, as the left ventricle 800 contracts during systole, the ventricular apex moves, e.g., forces upward and flattens to some degree. This flattening is translated to the contour of piezoelectric patch 106 in that the patch curvature straightens. Thus, the piezoelectric patch 106 flexes as it follows the movement of the ventricle, resulting in cyclic material strain of piezoelectric material within flexure area 112. As described above, this cyclic material strain generates an electrical field in a cyclic fashion. The electric field may be transmitted through piezoelectric patch 106 to the underlying tissue of the left ventricle 800 to apply electrical stimulation to the tissue for therapeutic effect. For example, electrical stimulation from the patch may be applied to an area of damaged tissue to support angiogenesis and treat CHF following AMI. Ranges of electrical properties related to effective electrical stimulation may vary. For example, depending on the underlying target anatomy, voltage and current applications may vary. Nonetheless, in an embodiment, electrical stimulation of underlying tissue over a period of about 1 day to 1 week or more with a generated current of between about 0.01 to 5 nA may be sufficient to effectively treat infarct tissue. Of course, higher currents, for example, in the range of about 10-50 µA may also provide effective therapy. These currents may correspond to electric field strengths, for example, of between about 0.1 to 10 V/cm. Accordingly, it will be appreciated that a medical implant in accordance with this disclosure may provide any range of electrical properties induced by the piezoelectric effect to electrically stimulate a target anatomy. It is also envisioned that the piezoelectric property of the implant material may change over time due to load-dependent alteration of the material ultrastructure, such as viscoelastic property due to polymer chain rearrangement or lattice property changes in inorganic piezoelectric crystal structure.

Piezoelectric patch 106 is configured to be delivered to, or placed on, a cardiac anatomy as described above, or on other anatomies. For example, piezoelectric patch 106 may be delivered into the vasculature. Alternatively, piezoelectric patch 106 may be delivered to, or placed on, a renal anatomy. Furthermore, piezoelectric patch 106 may be delivered to an intestinal anatomy, as described below. Thus, the medical implant 100 described herein may be suited to a variety of anatomies beyond the cardiac anatomy. In addition, the principles of the piezoelectric patch 106 may be leveraged into other device configured to achieve similar results in differing anatomies.

Figure 9:
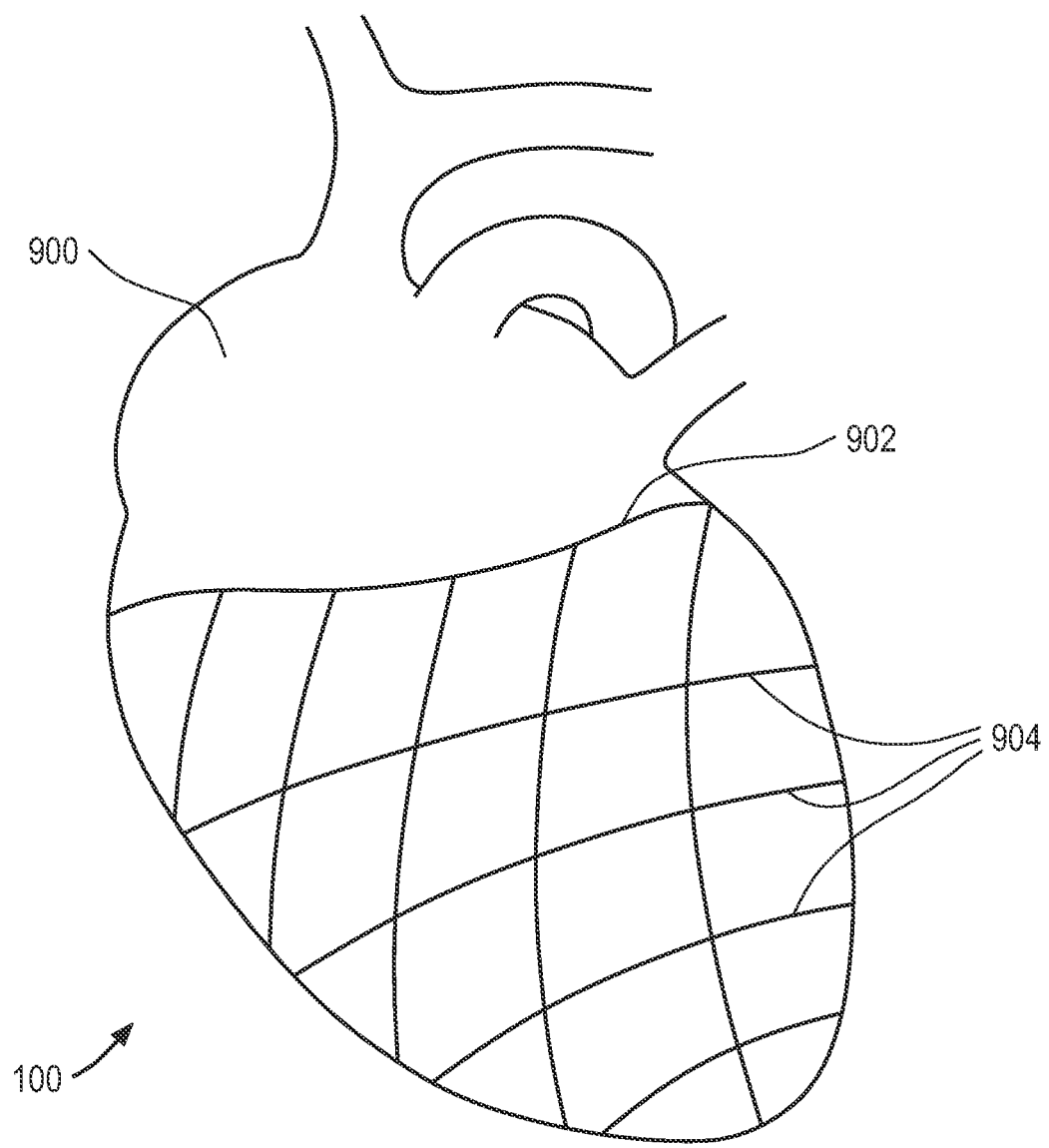
FIG. 9 is a perspective view of a medical implant placed around a heart in accordance with an embodiment of the invention.

Referring to FIG. 9, a perspective view of a medical implant placed around a heart is shown in accordance with an embodiment of the invention. An alternative embodiment of a device for effecting electrical stimulation as a pro-healing trigger includes a piezoelectric mesh 902 formed from one or more braid 904 of piezoelectric material. Braids 904 may be interwoven with each other, allowing for relative movement and sliding between braids, or braids 904 may be bonded at intersection points where a braid crosses another braid. For example, braids 904 may be adhesively or thermally bonded. Braids 904 may be sized to provide sufficient flexure under pressure provided by a target anatomy, but may also adequately constrain the underlying tissue. For example, braids 904 may be formed from a semi-elastic structure incorporating piezoelectric materials, and the structure may include thread diameters in the range of about 3 to 10 mm. Threads or fibers making up braids 904 may furthermore be woven into a mesh with exposed surface area between braids of between about 5 to 2500 mm$^2$. However, these dimensions are examples, and other mesh dimensions and/or geometry may be used within the scope of this disclosure.

Piezoelectric mesh 902 may include a piezoelectric material to generate electricity. For example, the piezoelectric material can be distributed within the device or coated or attached to the outside of the device, e.g., braid 904 material may be piezoelectric or braids 904 may be coated with piezoelectric material. In some embodiments, the piezoelectric material comprises a polymer. Thus, the piezoelectric material may generate voltage when stretched.

Piezoelectric mesh 902 may have a sac contour that closely resembles the shape of a target anatomy, such as the heart 900, and thus, the mesh 902 may be expanded and wrapped over the heart 900 surface during delivery. The mechanical mesh 902 may clamp around the heart 900 or left ventricle 800 such that the device restrains the heart 900 during ventricular diastole or atrial diastole, and in reaction, the mesh 902 may be strained by the heart 900 during systole. As with piezoelectric patch 106, cyclical straining of piezoelectric mesh 902 may result in electric field generation within piezoelectric mesh 902. Furthermore, electricity may be transferred to the underlying heart 900 tissue for electrical stimulation therapy of, e.g., infarcted tissue to treat CHF.

In an embodiment, piezoelectric mesh 902 acts as an extra-ventricular mechanical mesh 902 to limit diastolic expansion of the myocardium 402. For example, piezoelectric mesh 902 may provide a constraint to heart 900 and this constraint may act to scaffold heart 900, which may be helpful in treating CHF. Thus, the piezoelectric mesh 902 may support heart 900 without impeding the pumping of the heart 900. As a result piezoelectric mesh 902 may provide a dual therapy in that it may alleviate CHF by providing a supportive constraint and it may facilitate angiogenesis of infarcted tissue causing the CHF condition.

As with any of the medical implants 100 described, the size, shape, and structural characteristics may vary by application. Furthermore, the delivery devices and routes may vary. For example, in the case of an extra-ventricular mesh, piezoelectric mesh 902 may be suited for thoracoscopic delivery to heart 900.

Figure 10:
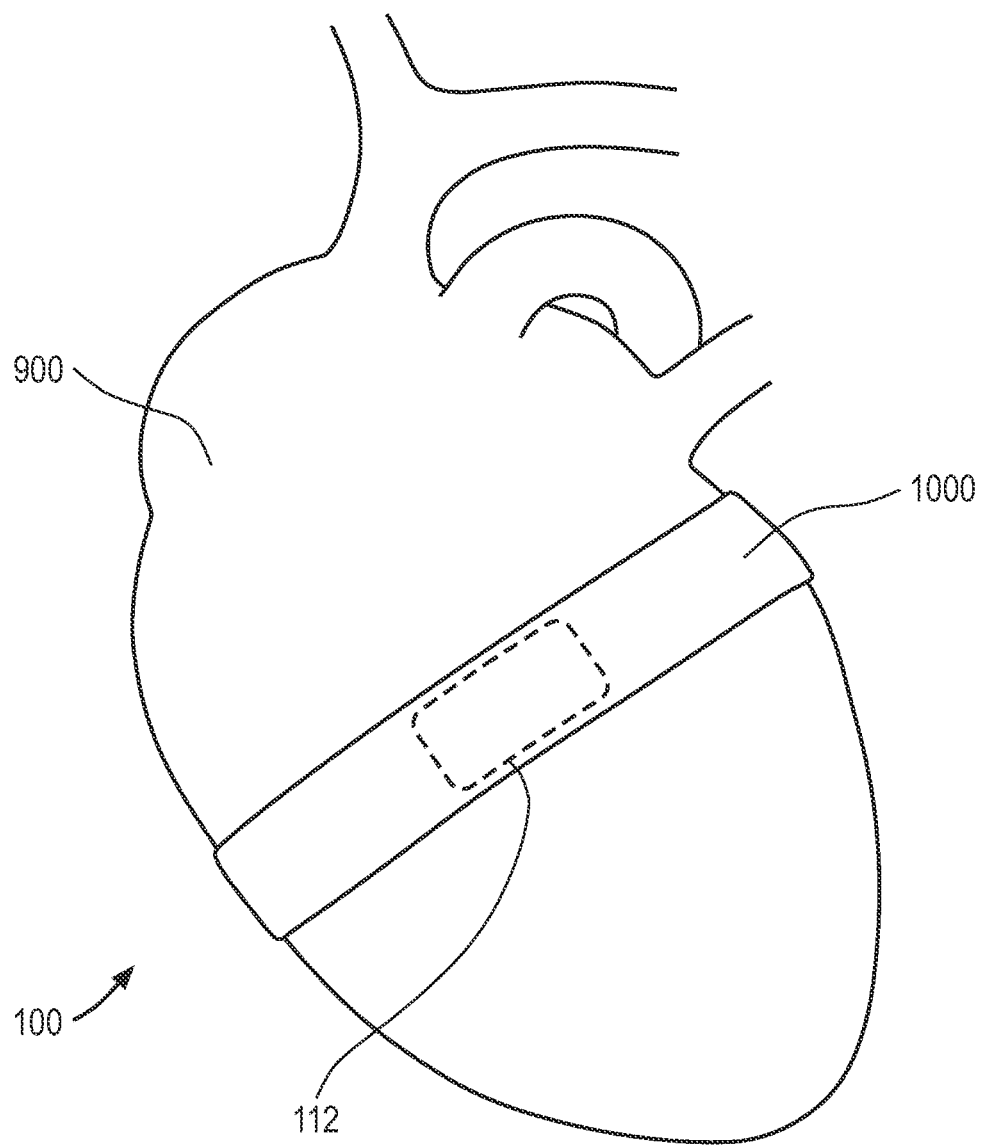
FIG. 10 is a perspective view of a medical implant placed around a heart in accordance with an embodiment of the invention.

Referring to FIG. 10, a perspective view of a medical implant placed around a heart is shown in accordance with an embodiment of the invention. Rather than place a piezoelectric mesh 902 over the entire heart surface, a girdle 1000 may be used to wrap around only a portion of heart 900. For example, girdle 1000 may be a band, a belt, a strap, or other structure with a length sufficient to wrap around the heart circumference at a target location. In one embodiment, a polymeric girdle 1000 may be made from material that can limit tension, but that is otherwise deformable to conform to the anatomical geometry of the recipient heart 900. Thus, piezoelectric girdle 1000 may constrain the dilatation of heart 900 during one segment of a heart beat, e.g., diastole, but may not constrain the action of the ventricle during another segment, e.g., systole. Girdle 1000 may be an elastic circular band with enough elasticity to permit it to be stretched over heart 900 and released to engage and constrain heart 900. Alternatively, girdle 1000 may initially be a strap with two ends, and the ends may be engaged in vivo, e.g., using a hook and loop fastener or other fastening system, to result in a circular band around the heart 900. As with piezoelectric mesh 902, implanted girdle 1000 may scaffold and support heart 900.

In an embodiment, girdle 1000 may include flexure area 112 that includes a piezoelectric material. Thus, in an embodiment, flexure area 112 may be less than entire surface area of girdle 1000 such that girdle 1000 applies electrical stimulation to a selected region of heart 900. As heart 900 pumps blood, flexure area 112 of girdle 1000 may stretch and relax, and thus flexure area 112 may undergo cyclic strain. Cyclic strain of flexure area 112 may generate electrical voltage that is directed from flexure area 112 to heart 900, thus applying electrical stimulation to the tissue of heart 900 to support angiogenesis of an underlying infarct area and to treat CHF.

Figure 11:
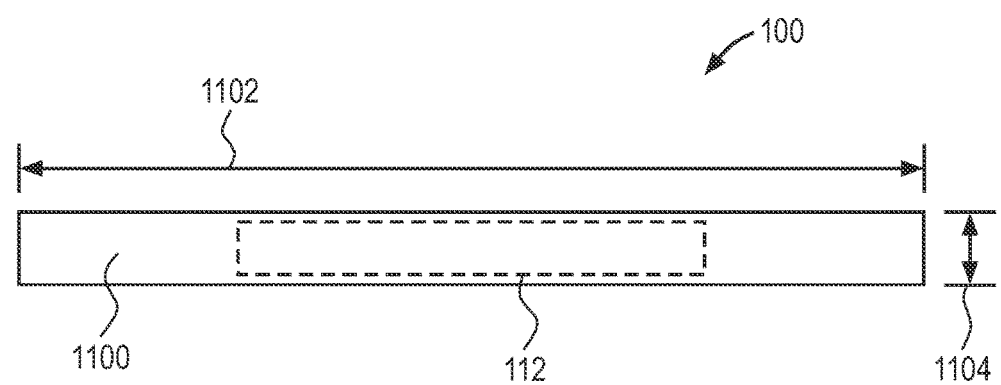
FIG. 11 is a top view of a medical implant in accordance with an embodiment of the invention.

Referring to FIG. 11, a top view of a medical implant is shown in accordance with an embodiment of the invention. Medical implant 100 may be a substantially flat material in the shape of an elongated ribbon, i.e., a piezoelectric strip 1100. Piezoelectric strip 1100 may have a substantially straight configuration. In some embodiments, the shape of piezoelectric strip 1100 is selected to customize a fit to a target anatomy. For example, a longer, thinner organ may have a matching, longer, thinner strip. Similarly, piezoelectric strip 1100 may have a shape that facilitates its connection to the surface of an organ. For example, piezoelectric strip 1100 may be shaped so that it wraps around the target organ to one degree or another.

Piezoelectric strip 1100 may include a length 1102 and a width 1104, and thus in an embodiment, piezoelectric strip 1100 may be substantially rectangular. As above, length 1102 and width 1104 of piezoelectric strip 1100 may be sized to match the target treatment zone. For example, length 1102 and width 1104 may each be 0.9 to 1.5 times the length and width of the target zone, respectively. The strip may thus have two ends that may be fastened in vivo to form a band. Ends may be fastened in vivo using mechanical fasteners, e.g., hook and loop, or other methods, e.g., adhesive or thermal welding. Piezoelectric strip 1100 may further include a first side and a second side defining a thickness therebetween, and the thickness may be less than 50%, 40%, 30%, 20%, or 10% of the length 1102 or width 1104 dimension.

Piezoelectric strip 1100 may include flexure area 112 capable of generating electricity in response to mechanical strain. In various embodiments, flexure area 112 includes a piezoelectric material, such as a poled polymeric material with piezoelectric behavior. Alternatively, the material can itself be an aggregate of materials that substantially exhibit a piezoelectric effect and materials that do not substantially exhibit a piezoelectric effect, yet where overall the piezoelectric effect remains.

In various embodiments, ribbon is configured to attach to the outside of a mammalian organ or configured for insertion into one or more cavities inside of a mammalian organ. For example, piezoelectric strip 1100 may include one or more anchor 200 to facilitate attachment to a target anatomy. In these or other embodiments, ribbon is configured to be placed within a membrane or sac surrounding a mammalian organ.

In some embodiments, configured for insertion into one or more cavities inside of a mammalian organ means that ribbon is constructed to be flexible enough to fit into the cavity. In some embodiments, ribbon is constructed to be flexible enough to fit through naturally existing passageways connected to the cavity. In some embodiments, ribbon is designed to be deliverable to the outside of the organ using an appropriate delivery method. For example, depending on the target anatomy, piezoelectric strip 1100 may be delivered via percutaneous, subxiphoid, laparoscopic, or endoscopic devices and routes.

Figure 12:
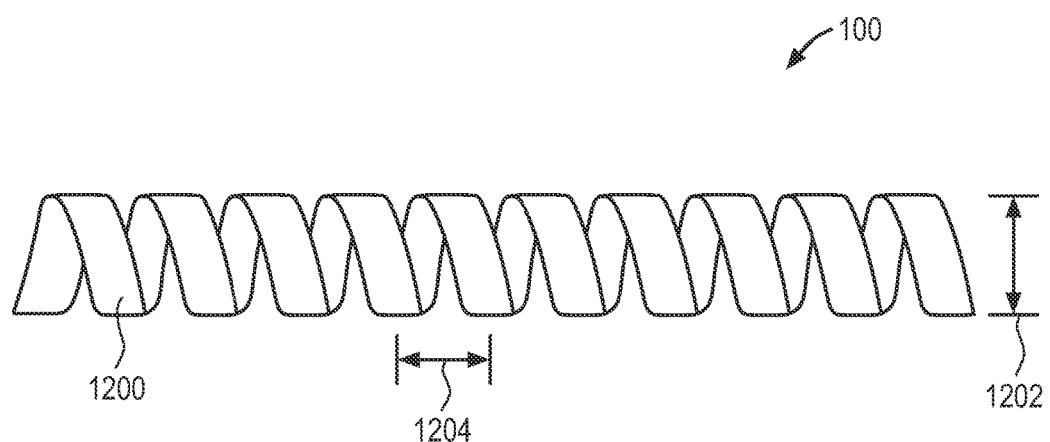
FIG. 12 is a side view of a medical implant in accordance with an embodiment of the invention.

Referring to FIG. 12, a side view of a medical implant is shown in accordance with an embodiment of the invention. Medical implant 100 may be a substantially flat material, such as piezoelectric strip 1100, transformed into a helix to form piezoelectric coil 1200. In some embodiments, the shape of piezoelectric coil 1200 may be selected to fit to a target anatomy. For example, piezoelectric coil 1200 may be formed to have a length and diameter that matches an inner diameter and length of a target coronary vessel. Alternatively, piezoelectric coil 1200 may be formed to have a length and diameter 1202 that matches an inner diameter and length of a target ileum. Furthermore, piezoelectric coil 1200 may be configured to be deployed within an inner diameter of a lumen or organ, or to be wrapped around an external surface of the target anatomy. For example, in the case of internal deployment, piezoelectric coil 1200 may act like a stent to radially support a vessel. Thus, piezoelectric coil 1200 may include a helix with a shape that facilitates its interaction with the surface of an organ. Alternatively, piezoelectric coil may be formed in the shape of a stent having sinusoidal stent rings interconnected by various links and/or connectors, as is well known in the art.

In an embodiment, piezoelectric coil 1200 may include a material that acts as an effective piezoelectric material, such as a poled polymeric material with piezoelectric behavior. Alternatively, the material can itself be an aggregate of materials that substantially exhibit a piezoelectric effect and materials that do not substantially exhibit a piezoelectric effect, yet where overall the piezoelectric effect remains.

In some embodiments, securement of piezoelectric coil 1200 relative to the target anatomy may be further aided with one or more anchor 200. For example, anchor 200 may include an adhesive, hook, barb, etc., to facilitate securing piezoelectric coil 1200 relative to a target tissue.

In an embodiment, piezoelectric coil 1200 may be flexible enough to fit into a cavity and/or fit through naturally existing passageways connected to the cavity. In some embodiments, piezoelectric coil 1200 may be delivered through a percutaneous, subxiphoid, laparoscopic, or endoscopic delivery system and/or route. For example, piezoelectric coil may be delivered percutaneously on a balloon element of a balloon catheter device. Flexibility of piezoelectric coil 1200 may be controlled by altering a pitch 1204 of piezoelectric coil 1200 to increase or decrease flexibility. Alternatively, helix thickness or material properties may be modified to control flexibility of piezoelectric coil 1200.

In an embodiment, all or a portion of the various medical implant 100 configurations described above may be formed from a biodegradable material. For example, a helical portion of piezoelectric coil 1200 may be formed from a biodegradable material such as poly (glycolic acid) or poly (lactic acid) polymers, or any other biodegradable material, including biodegradable metals such as iron and magnesium alloys. Within the helical portion, a flexure area 112 may exist that further includes a non-biodegradable piezoelectric polymer. Thus, portions of medical implant 100 may degrade gradually over time while remodeling of the target anatomy occurs. Following degradation an implanted piezoelectric flexure area 112 may be embedded within the remodeled lumen and continue to generate electricity even after the helix scaffold is absorbed by the body.

Further configurations for a medical implant 100 with piezoelectric characteristics may be envisioned by one skilled in the art. For example, in an embodiment, an intra-ventricular mechanical scaffold deployed by, for example, a PTCA procedure or a thoracoscopic procedure may serves as a left ventricular assist device to provide stress shielding of the left ventricle 800. In another embodiment, a shape memory net can be embedded into the left ventricle 800 such that, in the end or diastolic stage of the patient's heart beat, the net exerts a net tension on the ventricle to force the blood out through the aortic valve. Therefore, during the systolic cycle this force magnifies the wall force of the ventricle on the ventricular blood. Other device configurations may be embodied in devices that undergo mechanical strain as a result of the natural movement of an underlying target anatomy. Any of these devices may further include a flexure area 112 including a piezoelectric material that generates electricity in response to the anatomical motion. Thus, electrical stimulation may be provided to numerous anatomies using a medical implant 100 within the scope of this disclosure. Likewise, any of the devices may further include a heating element 300 to generate heat within a magnetic field. Thus, thermal therapy may be provided in addition to electrical stimulation in any of the embodiments. Similarly, drug depots 500 filled with therapeutic substances may also be used in any of the embodiments to provide supplemental drug therapy.

Figure 13:
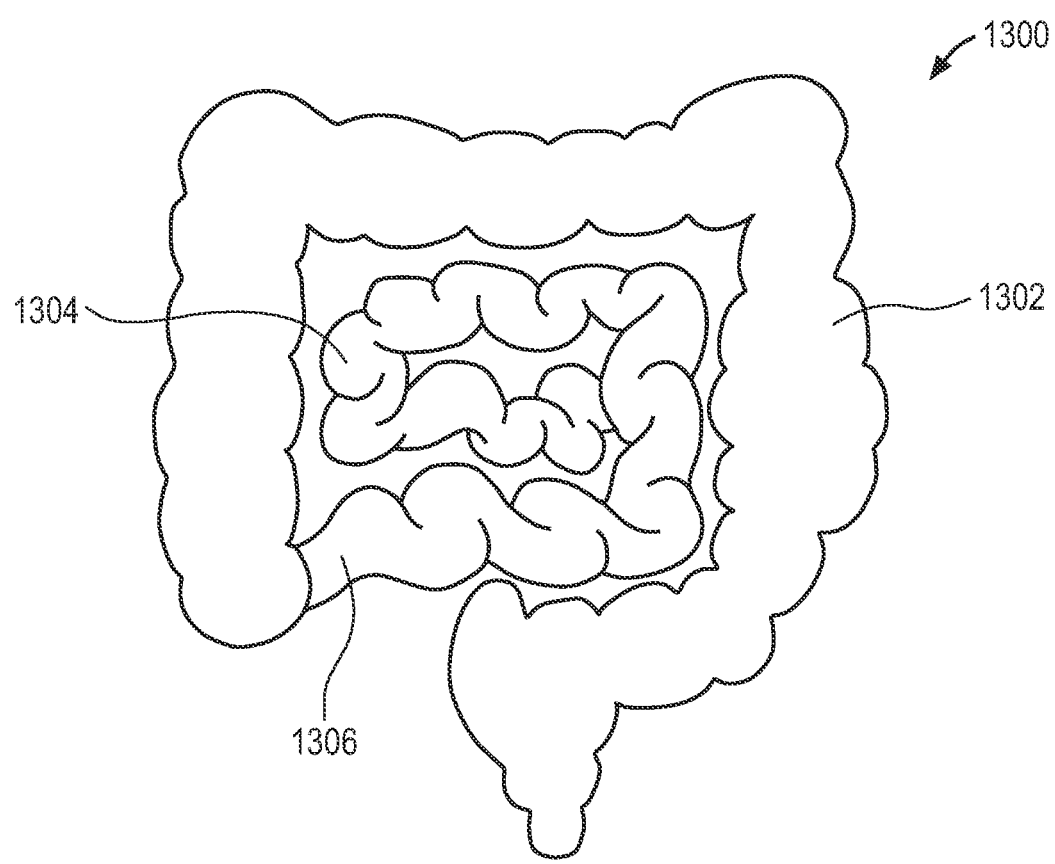
FIG. 13 is a pictorial view of an intestinal anatomy.

Referring to FIG. 13, a pictorial view of an intestinal anatomy is shown. Intestinal anatomy 1300 includes a large intestine 1302 and a small intestine 1304. Small intestine 1304 connects with a stomach near a proximal portion, and extends distally toward a connection with large intestine 1302 near an ileum 1306. Ileum 1306 adsorbs various enzyme molecules and absorbs products of digestion. Ileum 1306 also secretes various hormones into the blood. As discussed above, the release of small intestinal hormones is integral to postprandial responses that reduce food intake. Although the mechanism of action is debated, electrical stimulation of the ileum 1306 may provide a mechanism for controlling these postprandial responses.

Figure 14:
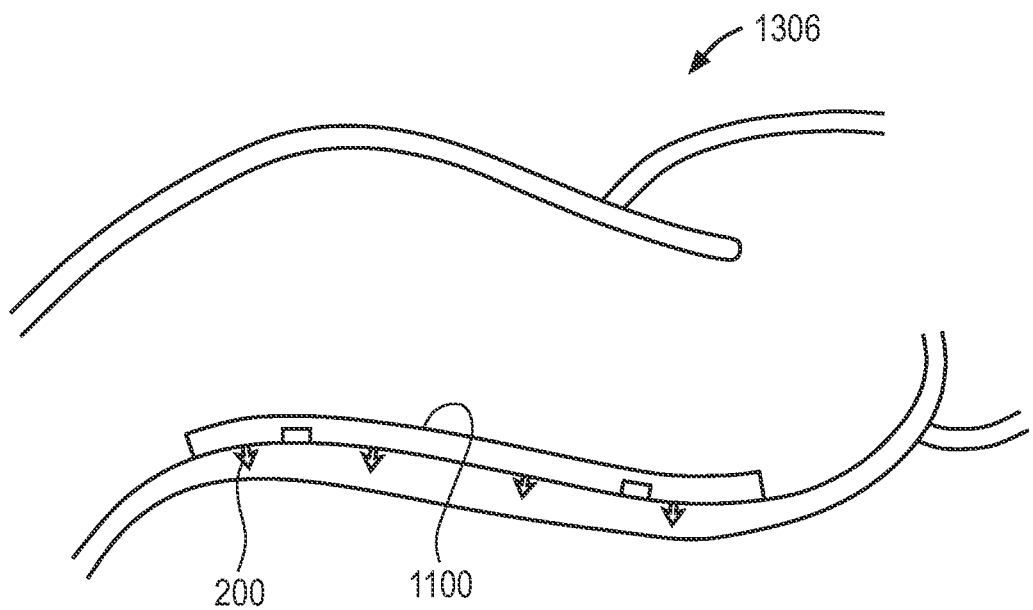
FIG. 14 is a cross-sectional view of a medical implant placed within an ileum of an intestinal anatomy in accordance with an embodiment of the invention.

Referring to FIG. 14, a cross-sectional view of a medical implant placed within an ileum of an intestinal anatomy is shown in accordance with an embodiment of the invention. To electrically stimulate the ileum 1306, any of the piezoelectric medical implants 100 described above may be sized and configured to be implanted in the intestinal anatomy 1300. For example, piezoelectric strip 1100 may be delivered into the ileum 1306 and placed on an inner surface of the ileum 1306.

As discussed above, piezoelectric strip 1100 may be substantially rectangular and may have a length 1102 aligned with an axis of ileum 1306. Alternatively, piezoelectric strip 1100 may be aligned equatorially around ileum 1306. In an embodiment, piezoelectric patch 106 may be used rather than piezoelectric strip 1100. The rectangular profile of piezoelectric strip 1100 and the circular, elliptical, or otherwise shaped profile of piezoelectric patch 106 may have similar minor axis 104 to major axis 102 ratios, e.g., ranging from about 1:1.1 to 1:50.

Piezoelectric strip 1100, or any medical implant 100 suited to intestinal anatomy 1300, may further include a flexure area 112 with a piezoelectric material for generating electricity in response to the peristaltic motion of intestinal anatomy 1300. Thus, peristaltic, pulsatile, or any other motion that causes bending, twisting, or flexing of flexure area 112 may result in electrical field generation. Electricity generated by piezoelectric strip 1100 may be transferred through piezoelectric strip 1100 to ileum 1306 to stimulate and/or control hormone secretion as a treatment for diabetes.

In an embodiment, piezoelectric strip 1100 may be delivered to any part of a patient's intestinal tract, as desired by a physician. For instance, piezoelectric strip 1100 may be delivered laparoscopically or otherwise to an inner or outer surface of ileum 1306. Alternatively, medical implant 100 may be delivered into intestinal anatomy 1300 endoscopically.

Figure 15:
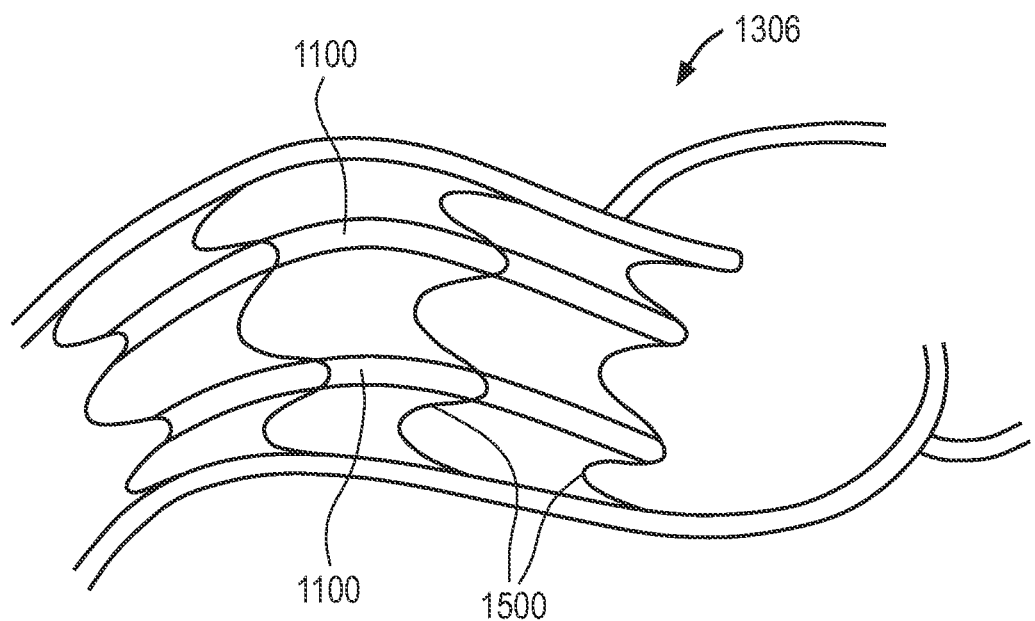
FIG. 15 is a cross-sectional view of a medical implant placed within an ileum of an intestinal anatomy in accordance with an embodiment of the invention.

Referring to FIG. 15, a cross-sectional view of a medical implant placed within an ileum of an intestinal anatomy is shown in accordance with an embodiment of the invention. As with cardiac applications, the intestinal anatomy 1300 lends itself to a variety of medical implant 100 configurations. For example, in an embodiment, one or more piezoelectric strip 1100 may be supported against an internal surface of ileum 1306 by one or more strut 1500. Strut 1500 may have a sinusoidal configuration, including various peaks and valleys, as known in the stent technology art. For example, struts 1500 may be ring-shaped and have an unexpanded and expanded diameter. Piezoelectric strips 1100 may be attached to one or more strut 1500, e.g., by an adhesive or thermal bond, and thus, piezoelectric strips 1100 may be axially aligned and include a smaller gap between each strip when struts 1500 are in an unexpanded configuration as compared to when struts 1500 are in an expanded configuration.

In an expanded configuration, struts 1500 may serve to hold piezoelectric strips 1100 against ileum 1306 without substantially impeding the peristaltic motion of ileum 1306. Thus, struts 1500 may be flexible and be able to resiliently compress and expand under pressure provided by the ileum 1306. In an embodiment, struts 1500 may be formed from nickel-titanium shape memory alloy having a width 1104 and thickness of about 0.003-inch to allow for the struts 1500 to be squeezed to a smaller diameter 1202 and relaxed to a larger diameter 1202. As a result of this squeezing or other peristaltic motion of the ileum 1306, piezoelectric strip 1100 between struts 1500 and ileum 1306 may undergo mechanical strain to generate electricity for electrical stimulation of the ileum 1306. This electrical stimulation may control hormone release as a treatment for diabetes.

Figure 16:
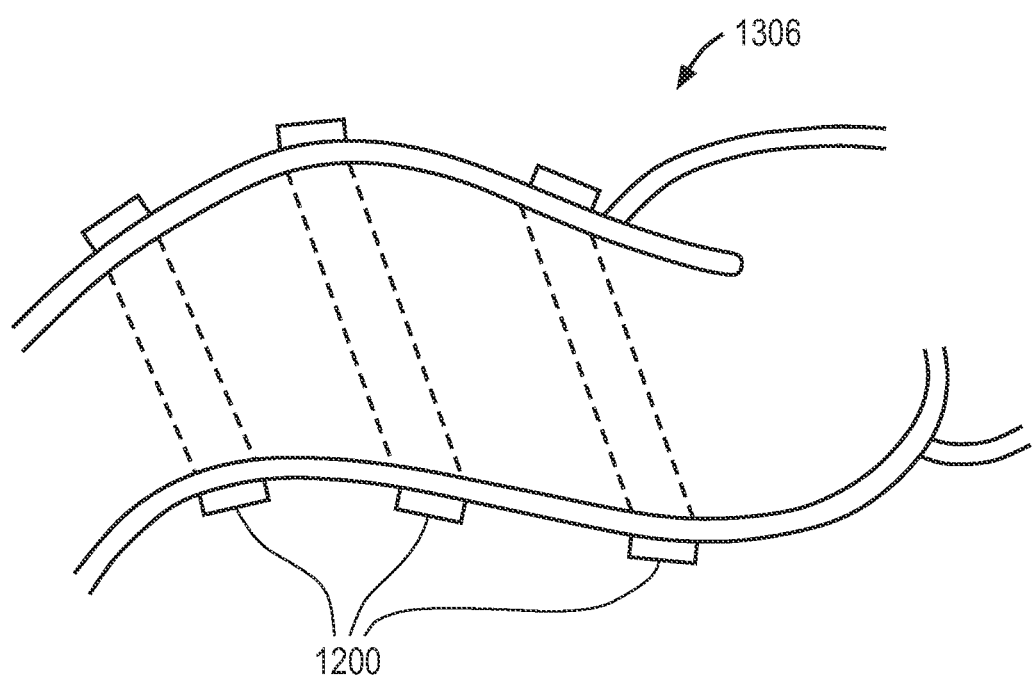
FIG. 16 is a cross-sectional view of a medical implant placed around an ileum of an intestinal anatomy in accordance with an embodiment of the invention.

Referring to FIG. 16, a cross-sectional view of a medical implant placed around an ileum of an intestinal anatomy is shown in accordance with an embodiment of the invention. Piezoelectric coil 1200 may be sized and shaped to be implanted over an external surface of ileum 1306. Piezoelectric coil 1200 may be formed with an inner diameter that is less than an outer diameter of ileum 1306, such that it will have a dimensional interference with ileum 1306 and tend to expand when wrapped around ileum 1306. Thus, in an embodiment, piezoelectric coil 1200 may be flexible enough so as not to constrain ileum 1306, but rather, to expand under the radial load provided by the interference with ileum 1306. Alternatively, piezoelectric coil 1200 may squeeze ileum 1306 to a smaller diameter in the interference locations, but piezoelectric coil 1200 may remain in place due to the gripping force caused by the interference. Pitch 1204 and length of piezoelectric coil 1200 may be sized to accommodate a target ileum length.

Once located over ileum 1306, piezoelectric coil 1200 may provide electrical stimulation to ileum 1306. More specifically, piezoelectric coil 1200 or a portion thereof may include piezoelectric material such as those described above. As the ileum 1306 undergoes peristaltic motion, piezoelectric coil 1200 wrapped around ileum 1306 may also move under, e.g., bending and tensile loading. Thus, piezoelectric material within piezoelectric coil 1200 may generate electricity, which may then be transferred to the underlying ileum 1306. Resultantly, hormone secretion of the ileum 1306 may be controlled in a manner that treats diabetes.

Piezoelectric coil 1200 may be formed from piezoelectric strip 1100 either during manufacture or during implantation. For example, during manufacture piezoelectric strip 1100 may be heat set and or molded into a helical configuration with a defined pitch 1204, diameter 1202, and length. Alternatively, during implantation, piezoelectric strip 1100 may be wrapped around an inner or outer diameter of a target anatomy. As piezoelectric strip 1100 is wrapped, one or more anchor 200 on piezoelectric strip 1100 may embed in the target anatomy tissue to secure piezoelectric strip 1100 and maintain the strip in a curved and/or helical configuration.

One of ordinary skill in the art will recognize that in an embodiment, piezoelectric coil 1200 may be placed such that digesting food moving through the intestinal anatomy 1300 does not displace piezoelectric coil 1200 as the food passes. In some embodiments, this displacement is resisted by anchors 200 on piezoelectric coil 1200. In other embodiments, this displacement is resisted by the natural resiliency of piezoelectric coil 1200 that presses against an inner surface of intestinal anatomy 1300. Thus, piezoelectric coil 1200 may be configured to remain in place and not be dislocated by the natural movement of food through the intestinal anatomy 1300.

Any of the devices described above may be delivered to a portion of intestinal anatomy 1300, which is subject to mechanical movement. The mechanical movement causes the devices to experience mechanical deformations or flexing. The movement causing this flexing comes from the patient's daily movement, the peristaltic movement of the patient's intestinal anatomy 1300, or both. Any movement, whether from internal body processes or external movement transmitted into the device may generate some piezoelectric effect in a flexure area 112 having piezoelectric material. The motion may cause the generation of local electric fields close to the intestinal tissue. It is hypothesized that electric fields cause the tissue to generate increased amounts of GLP-1, and thus, mechanical strain of medical implant 100 caused by intestinal anatomy 1300 may result in control of hormone secretion and treatment of diabetes.

It is contemplated that embodiments of medical implant 100 that are delivered into intestinal anatomy 1300 may also be configured to block uptake of food. When placed near the beginning of the small intestine 1304, piezoelectric patch 106, piezoelectric strip 1100, or piezoelectric coil 1200 may act to prolong the uptake of carbohydrates. This prolonged uptake may influence diabetic symptoms. Moreover, combining the food-blocking effect from these medical implants 100 with the raised GLP-1 levels from electrical stimulation provided by the piezoelectric material may combine to simultaneously influence diabetic symptoms through two different pathways. Furthermore, in the case of medical implants 100 having biodegradable polymers, the biodegradation of such polymers near the ileum 1306 may also raise GLP-1 levels to treat diabetes. Thus, just as a device configuration having combined thermal and piezoelectric effects may be used to treat CHF in multiple ways, a device may be configured to treat diabetes in multiple ways as well.

As discussed above, embodiments of the invention that employ a drug can use any drug or combination of drugs useful for treating diseases in humans. For instance, the compositions of the invention are suited for combining with one or more hypertension drugs, one or more high-cholesterol or triglyceride-treating drugs, or any combination of hypertension drugs and high-cholesterol or triglyceride-treating drugs. Further listings of drugs that may be used with a medical implant 100 within the scope of the present invention are shown below. Despite the extensive listing of drugs provided, the below itemization is not intended to be limiting of the scope of drugs that are suitable for use.

Drugs for treating cardiac conditions may include: growth factors, polynucleotides encoding growth factors, angiogenic agents, calcium channel blockers, antihypertensive agents, antimitotic agents, inotropic agents, antiatherogenic agents, anti-coagulants, β-blockers, anti-arrhythmic agents, anti-inflammatory agents, vasodilators, thrombolytic agents, cardiac glycosides, antibiotics, antiviral agents, antifungal agents, agents that inhibit protozoans, angiotensin converting enzyme (ACE) inhibitors, brain natriuretic peptide (BNP), antineoplastic agents, and steroids.

The following classes of drugs are used to treat hypertension: angiotensin-converting enzyme (ACE) inhibitors, angiotensin ii receptor blockers, beta blockers, calcium channel blockers, renin inhibitors, and thiazide diuretics.

The following drugs are used to treat hypertension: acebutolol, aceta-zolamide, aliskiren, amiloride and hydrochlorothiazide, amiloride hydrochloride, amlodipine, amlodipine and benazepril, atenolol, atenolol and chlorthalidone, benazepril, benazepril and hydrochlorothiazide, betaxolol, bisoprolol, bisoprolol and hydrochlorothiazide, bumetanide, candesartan, captopril, captopril and hydro-chlorothiazide, carteolol, carvedilol, chlorthalidone, clonidine, diltiazem, doxazosin, enalapril, enalapril and hydrochlorothiazide, esidrix, ethacrynic acid, felodipine, felodipine and enalapril, fosinopril, furosemide, guanabenz, guanfacine, hydralazine, hydralazine and hydrochlorothiazide, hydrochlorothiazide, indapamide, irbesartan, isradipine, labetalol, lisinopril, lisinopril and hydrochlorothiazide, losartan, losartan and hydrochlorothiazide, methyldopa, methyldopa and hydrochlorothiazide, metolazone, metoprolol, metoprolol and hydrochlorothiazide, microzide, moexipril, nadolol, nadolol and bendroflumethiazide, nicardipine, nifedipine, nisoldipine, olmesartan, penbutolol, prazosin, propranolol, propranolol and hydrochlorothiazide, quinapril, ramipril, reserpine, spironolactone, spironolactone and hydrochlorothiazide, telmisartan, terazosin, timolol, torsemide, trandolapril, triamterene, tri-amterene and hydrochlorothiazide, valsartan, verapamil, verapamil (extended release), and trandolapril.

The following classes of drugs are used to treat high cholesterol or high triglycerides: lovastatin, simvastatin, atorvastatin, fluvastatin, pravastatin, rosuvas-tatin, fenofibrate, ezetimibe, niacin, fenofibric acid, bile acid sequestrants, omega-3-acid ethyl esters, cholestyramine resin, colesevelam hydrochloride, red yeast rice, gemfibrozil, evening primrose oil, cerivastatin, clofibrate, dextrothyroxine sodium, and pitavastatin.

Renal drugs may include substances exhibiting a property to inhibit a biological process contributing to nephropathy. Such biological processes may include, but are not limited to, changes in glomerular basement membrane, changes in mesangial matrix deposition and podocyte attachment or apoptosis.

The selected drug may have a property to inhibit undesirable effects of the renin-angiotensin system in the kidneys. The renin-angiotensin system responds to a decrease in the perfusion of the juxtaglomerular apparatus found in afferent arterioles of the glomerulus of the kidney by constricting glomerular arterioles. Such constriction causes blood to build up in the glomerulus and increase glomerular pressure. Representative drugs that may act to inhibit this process include, but are not limited to, angiotensin converting enzyme (ACE) inhibitors, angiotensin receptor blockers (ARBs), and renin inhibitors.

Useful drugs are those that inhibit protein kinase C. Representative drugs may include, but are not limited to, ruboxistaurin (LY333531), enzastaurin (LY317615), bisindolylmaleimide IX, chelerythrine, edelfosine, edelfosina, ET180CH3, H-7, HA-100, H89, HA-1004, Ro 31-8220, rottlerin, staurosporine, and quercetin.

The transforming-growth-factor-beta system contributes to the progression of renal damage due to stimulation of extracellular matrix deposition. Thus, in some embodiments, the treatment agent may include an agent having a property to inhibit transforming growth factor beta, its receptor and SMAD and other signaling molecules downstream of the receptor. Representative inhibitors may include, but are not limited to antisense molecules, ribozymes, siRNA, antibodies, receptor kinase inhibitors and other small molecule inhibitors such as halofuginone, sirolimus, everolimus, biolimus, ABT578 and nuclear receptor agonists such as estradiol, retinoids, and peroxisome proliferator-activated receptors (PPAR) agonists.

Antineoplastic or antimitotic examples include: paclitaxel, docetaxel, metho-trexate, Azathioprine, Vincristine, Vinblastine, Fluorouracil, doxorubicin hydrochlo-ride, and mitomycin.

Antiplatelet, anticoagulant, antifibrin, and antithrombin examples include: Heparinoids, Hirudin, Argatroban, Forskolin, Vapiprost, Prostacyclin, prostacyclin analogues, Dextran, D-phe-pro-arg-chloromethylketone (synthetic antithrombin), Dipyridamole, glycoprotein IIb/IIIa platelet membrane receptor antagonist antibody, and recombinant hirudin and thrombin inhibitors.

The drug may also include cytostatic or antiproliferative agents, angiopeptin, angiotensin converting enzyme inhibitors, cilazapril, lisinopril, actinomycin D, dactinomycin, acti-nomycin IV, actinomycin I1, actinomycin X1, actinomycin C1, and actinomycin D derivatives or analogs.

Other potential drugs include: calcium channel blockers, nifedipine, colchicines, fibroblast growth factor (FGF) antagonists, omega 3-fatty acid, fish oil, flax seed oil, histamine antagonists, monoclonal antibodies (such as those specific for platelet-derived growth factor (PDGF) receptors), nitroprus side, phosphodiesterase inhibitors, prostaglandin inhibitors, suramin, serotonin blockers, steroids, thioprotease inhibitors, triazolopyrimidine (a PDGF antagonist), nitric oxide, alpha-interferon, genetically engineered epithelial cells, antibodies such as CD-34 antibody, abciximab (REOPRO), progenitor cell capturing antibody, prohealing therapeutic substances (that promotes controlled proliferation of muscle cells with a normal and physiologically benign composition and synthesis product), enzymes, anti-inflammatory agents, antivirals, anticancer drugs, anti-coagulant agents, free radical scavengers, estradiol, steroidal anti-inflammatory agents, non-steroidal anti-inflammatory dexamethasone, clobetasol, aspirin, Antibiotics, nitric oxide donors, super oxide dismutases, super oxide dismutase mimics, 4-amino-2,2,6,6-tetramethylpiperidine-1-oxyl (4-amino-TEMPO), Tacrolimus, Rapamycin, rapamycin derivatives 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, Zotarolimus™, and cytostatic agents.

The following summarizes some of the experiments that have been performed to develop the embodiments provided herein. The description is illustrative, however, and not exhaustive of the scope and results of experimentation performed thus far.

PVDF Film

PVDF film made from Kynar® 740 resin was obtained. Two thicknesses of the film were sampled, 0.002" and 0.005". In Table 1, key physical properties of the PVDF are listed for information purposes. The values from Table 1 were obtained from the product specification sheet provided by the manufacturer. The property results were obtained using ASTM test methods, and for the melt temperature differential scanning calorimetry (DSC) was used.

TABLE 1

Physical Properties of 0.002" and 0.005" Kynar ® PVDF

| Property | Units | Test Method | Result |
|---|---|---|---|
| Surface Resistivity | Ohms | ASTM D257 | >1016 |
| Dielectric Constant | 1 kHz | ASTM D150 | 8.15-10.46 |
| Tensile Strength | PSI | ASTM D882 | 7,550 |
| Melt Temperature | ° F. | DSC | 329-338 |
| Water Absorption @ 24 Hrs. | % | ASTM D882 | 0.01 |

Tensile testing equipment was used to induce a piezoelectric effect in the PVDF, the resulting current was measured using a picoammeter with the ability to detect current from the picoamp ($10^{-12}$) range to the milliamp ($10^{-3}$) range. The PVDF was expected to generate a current in the picoamp range when stressed. The cable used for the input was a standard RG-58 coaxial cable with a BNC (Bayonet-Neill-Concelman) connector. The other end of the coaxial cable was split and the positive and negative leads were separated. The separated leads were soldered to alligator clips and then wrapped with electrical tape. To verify that the leads were soldered properly, the leads were connected to an alkaline 9V battery to verify the picoammeter would produce a reading. With the leads connected to the 9V battery, the picoammeter read a current of 176±3 mA. However, in this application, using Ohm's Law a current of about 180 mA should be expected based on the 50Ω impedance of the RG-58 coaxial cable. The observed current of 176±3 mA showed that the leads were soldered correctly to the alligator clips. And the amperage measurement achieved a value close to the expected value of 180 mA indicating that the picoammeter was operating correctly.

For the purpose of this experiment, the tensile test equipment was used to repetitively stress the PVDF. These experiments used test equipment with a toggle switch that controlled the instrument's function. The idea was to load the PVDF sample into the tensile tester and use the toggle switch to quickly turn the pull feature on and off. Repetitively toggling the switch imparted an oscillatory stress on the PVDF, theoretically inducing a piezoelectric effect.

To prepare the sample of PVDF, thin strips were cut using standard scissors for both the 0.002" and 0.005" thicknesses. The approximate dimensions of the strips were 0.25"×4.0" for each. Once the samples were cut, the strips were loaded lengthwise into the grippers of the test equipment. The grippers were clamped very securely so that the PVDF would not slip. After the sample was successfully loaded, the toggle button was pressed and held down to allow the tensile tester to start pulling. The initial pull created enough tension on the PVDF to make it rigid before connecting the leads from the picoammeter. With sufficient tension on the PVDF, the leads from the picoammeter were attached.

The first experiment was conducted for both the thicknesses of the PVDF. Each sample was loaded correctly. For the experiment, the toggle button was repeatedly pressed and values were recorded from the ammeter concurrently every 15 seconds. The process was repeated until the PVDF began to neck, then the experiment was ended. Results of the test are provided below.

TABLE 2

Results of First Pull Test, 0.002" Thickness

| Time (Seconds) | Recorded Current (nA) |
|---|---|
| 0 | 0.0193 |
| 15 | 0.0242 |
| 30 | 0.0186 |
| 45 | 0.0098 |
| 60 | 0.0184 |
| 75 | 0.0203 |
| 90 | 0.0168 |

TABLE 3

Results of First Pull Test, 0.005" Thickness

| Time (Seconds) | Recorded Current (nA) |
|---|---|
| 0 | 0.0165 |
| 15 | 0.0211 |
| 30 | 0.0197 |
| 45 | 0.0301 |
| 60 | 0.0084 |
| 75 | 0.0176 |
| 90 | 0.0192 |

The results of a first pull test indicate a piezoelectric effect was produced when the toggle button was pressed. The difference in thickness did not appear to have any effect on the produced current. To ensure the results of the first pull test have merit, an additional test of the same method was conducted. The results of the second pull test are provided below.

TABLE 4

Results of Second Pull Test, 0.002" Thickness

| Time (Seconds) | Recorded Current (nA) |
|---|---|
| 0 | 0.0097 |
| 15 | 0.0142 |
| 30 | 0.0186 |
| 45 | 0.0098 |
| 60 | 0.0184 |
| 75 | 0.0203 |
| 90 | 0.0168 |

TABLE 5

Results of Second Pull Test, 0.005" Thickness

| Time (Seconds) | Recorded Current (nA) |
|---|---|
| 0 | 0.0188 |
| 15 | 0.0139 |
| 30 | 0.0231 |
| 45 | 0.0203 |
| 60 | 0.0194 |
| 75 | 0.0201 |
| 90 | 0.0172 |

The results of the second pull test confirmed the results of the first pull test: a piezoelectric effect was produced as a result of toggling the pull tester. Thus, a piezoelectric effect can be induced in PVDF.

Stretching PVDF Films

PVDF stretching was performed using a tensile testing apparatus enclosed in a temperature-controlled chamber at 85° C. The PVDF films were 0.010" thick, 3" wide, and 5" long. The films were stretched 3, 4, 5, and 6 times the original length. Each film was clamped into the apparatus, the chamber was heated, and the film was stretched at a rate of 1 mm/sec until the desired length was reached. The film was then removed and placed in an oven at 120° C. for 24 hours, then removed and left at room temperature for the quenching processes. Stretching films in the 4-6× range yielded much larger coefficient values than the 3× film, thus the 4-6× stretched films were compared to unmanipulated PVDF films. Current charge coefficient and voltage charge coefficient were calculated and used to compare the resultant post-stretching piezoelectric activity. Results from these stretched films revealed that stretching alone did not significantly raise the charge coefficient values. Stretching the film 6× the original length raised the charge coefficient 41% for the current measurement mode and lowered the charge coefficient 48% for the voltage measurement mode. Stretching the film 5×, 4×, and 3× actually lowered the charge coefficient significantly. These results indicate that stretching procedure alone may have minimal effect on the piezoelectric activity of PVDF film.

Poling PVDF Films

Poling of PVDF film was performed via a previously documented method. See Marcus, M. A., *Pseudo-AC Method of Nonuniformly Poling a Body of Polymeric Material and Flexure Elements Produced Thereby*. 1982, Eastman Kodak Company: United States of America. An electric field was applied across the thickness of the material inducing a non-uniform polarization. The apparatus used a temperature-controlled paraffin oil bath to avoid dielectric breakdown of the film. The PVDF film, with copper electrodes attached, was placed on the apparatus between the toggle clamps and the base plate and immersed in the oil bath. After poling with a high voltage power supply, the un-poled ends of the sample were cut off and the remaining portion was assessed for piezoelectricity. The results of poling alone were similar to only stretching; there was no significant effect on the piezoelectric charge coefficients of PVDF. Poling the unmanipulated film at 7 kV actually lowered the charge coefficients by 20%.

Stretching and Poling PVDF Films

PVDF films were treated by both stretching and poling. Films were stretched at 4× and poled at 5 kV, which produced an increase of 143% and 163% for the current and voltage measurement modes, respectively. A significant jump was also seen at 5× and 7 kV for a 551% increase in the current measurement mode and 2246% increase in the voltage measurement mode. The samples with the highest charge coefficients were those that were both stretched and poled. In general, stretching the film to at least 5×, combined with poling under at least 5 kV, appears to significantly increase the piezoelectric properties of PVDF films.

Piezoelectric Cell Studies

This example shows the culturing of endothelial cells with the piezoelectric inducing apparatus. The purpose of this test was to determine if endothelial cells can be cultured with the piezoelectric inducing apparatus. The test consisted of comparing the PVDF culture dish under piezoelectric conditions against two other dishes: a PVDF culture dish under static conditions and a regular polystyrene culture dish. The test was conducted twice: first, allowing cells to culture for 24 hours, and second, with the cells culturing for 72 hours. The samples were flexed to generate an electric field through the base material's piezoelectric properties.

A 24-hour experiment to investigate piezoelectric induced cell culturing was performed. Cells that were thawed for this experiment were Human Umbilical Vein Endothelial Cells (HUVEC) at their seventh passage. The thawed cells were harvested from a 75-cm² tissue culture flask supplemented with 20 mL of Endothelial Cell Media (ECM). The cells were maintained overnight in an incubator at 37° C. and under a humidified atmosphere of 5% $CO^2$. The ECM was aspirated off 24 hours after seeding to remove any non-adherent material and replaced with 12 mL of fresh ECM and allowed to grow to confluence. Three culture dishes sterilized by EtO were used for the experiment: a first dish as a control, consisting of a Polystyrene Culture Dish, a second dish as a PVDF control, consisting of a PVDF Culture Dish, and a third dish representing a PVDF culture dish with stimuli.

Each dish was supplemented with 20 mL of ECM and seeded, approximately 33% confluent, with 19,000 cells per cm². The hole where the cells were seeded for the PVDF Control and PVDF w/Stimuli dish was covered with a breathable Band-Aid to reduce contamination. The Control Dish (Dish 1), and the PVDF Control Dish (Dish 2), were allowed to incubate statically. The PVDF w/Stimuli the Dish (Dish 3), was secured into the piezoelectric inducing apparatus and was allowed to incubate statically for an hour at which time the piezoelectric effect was induced. The cells were maintained for 24 hours in an incubator at 37° C. and under a humidified atmosphere in 5% CO2. After 24 hours of incubation, the ECM was aspirated off each dish. For the polystyrene dish, 6 mL of histochoice was immediately added to fix the cells. For the PVDF culture dishes, the PVDF was carefully cut off using a razor and placed into a standard culture dish with 6 mL of histochoice. The cells were allowed to sit overnight in the histochoice solution. The following day the histochoice was removed and 6 mL of Bisbenzimide (BBI) (HOCHST dye #33258, vendor Invitrogen, Cat # H1398) was added to each sample to stain the cells. The contents from each well were observed under a fluorescent microscope at 4× magnification. Various regions were inspected for each sample. The samples were divided into thirds, and from those thirds each were inspected in three locations for cell attachment and confluence.

A 72-hour experiment was performed to investigate the effect of prolonged piezoelectric effect on cell culturing. The 72-hour experiment was conducted using the same methods described for the 24-hour experiment, except this experiment went for 72 hours.

The results were determined by visually assessing the percent confluence of each sample. To get a more representative estimate, each sample was divided into thirds and inspected in three different regions for confluence. The results from the 24-hour experiment indicated that a piezoelectric effect influenced the adhesion of endothelial cells.

The experiment indicates that endothelial cells were the most confluent on the polystyrene culture dish. However, after the 24-hour mark, the results indicate that the piezoelectric effect may have influenced endothelial cell proliferation as it was observed that the overall percent confluence of piezoelectric PVDF culture was greater than the overall percent confluence of the static PVDF culture dish.

The results from the 24-hour batch are promising with the greater overall percent confluence of the piezoelectric dish compared to the static dish. However, the 72-hour experiment was performed to determine if the duration of incubation increased or decreased the adherence of cells. Results after 72 hours indicated that duration positively affected the adherence of endothelial cells. Furthermore, the results also indicate the piezoelectric effect positively influenced the confluence of endothelial cells. The results are provided below in Tables 6.1 to 6.3.

TABLE 6.1

Experimental Results from 24-Hour Culture for Dish 1

| Dish 1 - Control | | % Confluence |
|---|---|---|
| First | Region 1 | 90 |
| | Region 2 | 95 |
| | Region 3 | 100 |
| Second | Region 1 | 95 |
| | Region 2 | 95 |
| | Region 3 | 90 |
| Third | Region 1 | 100 |
| | Region 2 | 100 |
| | Region 3 | 95 |
| Average | N/A | 95.5 |

TABLE 6.2

Experimental Results from 24-Hour Culture for Dish 2

| Dish 2 - PVDF Control | | % Confluence |
|---|---|---|
| First | Region 1 | 10 |
| | Region 2 | 15 |
| | Region 3 | 25 |
| Second | Region 1 | 15 |
| | Region 2 | 10 |
| | Region 3 | 20 |
| Third | Region 1 | 10 |
| | Region 2 | 10 |
| | Region 3 | 30 |
| Average | N/A | 16.1 |

TABLE 6.3

Experimental Results from 24-Hour Culture for Dish 3

| Dish 3 - PVDF w/Stimuli | | % Confluence |
|---|---|---|
| First | Region 1 | 20 |
| | Region 2 | 25 |
| | Region 3 | 25 |
| Second | Region 1 | 55 |
| | Region 2 | 70 |
| | Region 3 | 20 |
| Third | Region 1 | 30 |
| | Region 2 | 15 |
| | Region 3 | 20 |
| Average | N/A | 31.1 |

Based on the overall percentage of confluence, the piezoelectric dish outperformed the statically cultured PVDF dish. The degree to which the cells out-performed the static PVDF was also greater due to the longer duration of incubation. For the 24-hour experiment, the overall percent confluence of PVDF w/Stimuli dish (Dish 3) was 15 percent greater than the overall percent confluence of the PVDF Control dish (Dish 2). Over the 72-hour incubation period, the overall percent confluence increased 6.1 percent to 21.1.

The apparatus had the ability to induce piezoelectric effect on the culture dish, the culture dish had the ability to successfully contain media, and the apparatus was able to be placed inside an incubator for incubation. From a functional perspective, the experiment attempted to address two main questions: whether endothelial cells can be cultured with the piezoelectric inducing apparatus, and whether a piezoelectric effect influences the adhesion of the endothelial cells. From a qualitative standpoint, the results do suggest a piezoelectric effect positively influenced the adhesion of endothelial cells. A greater overall percent confluence of the PVDF w/Stimuli dish compared to the PVDF Control dish was seen in both the 24- and 72-hour experiments.

Intestinal Stimulation by Electrical Field Stimulation

An experiment to test whether intestinal stimulation by electrical field stimulation (EFS) directly alters local hormone release was performed using isolated rat distal ileum. GLP-1 released in the presence or absence of linoleic acid (LA) and electrical field stimulation was measured. Intact segments were oriented longitudinally between bipolar stimulating electrodes in organ-bath chambers containing modified Krebs-Ringers bicarbonate (KRB) buffer including protease inhibitors. Incubation in LA for 45 min increased GLP-1 concentration. Eleven electrical stimulation conditions were tested.

In the presence of LA, none of the stimulation conditions inhibited LA-evoked GLP-1 release, whereas two high frequency, short pulse widths and one low frequency long pulse width EFS condition enhanced LA-evoked GLP-1 release by >250%. These results are consistent with a local effect of intestinal electrical stimulation to enhance GLP-1 release in response to luminal nutrients in the intestines. In animal models, reduction of Glucagon receptors was shown to have controlled hyperglycemia even with impaired insulin secretion. Thus, the experiment indicates that, under certain conditions, electrical stimulation of locally isolated rat distal ileum can result in increased release of GLP-1. It follows that electrical stimulation may also enhance hormone release and provide a potential treatment for medical conditions such as diabetes or obesity in humans.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A medical implant comprising:
a piezoelectric patch having a flexure area to undergo mechanical strain caused by a target anatomy;
an anchor to secure the flexure area to the target anatomy; and
a heating element coupled to the piezoelectric patch, wherein the heating element is at least partially within the piezoelectric patch, and wherein the heating element is configured to generate heat in response to an oscillating electromagnetic field induced by an external source.

2. The device of claim 1, wherein the flexure area includes a piezoelectric polymer.

3. The device of claim 2, wherein the piezoelectric polymer includes a poled polymer.

4. The device of claim 3, wherein the poled polymer includes poly(vinylidene difluoride) (PVDF).

5. The device of claim 4, wherein the anchor includes one or more barbs to secure the flexure area to the target anatomy.

6. The device of claim 4, wherein the anchor includes an adhesive to secure the flexure area to the target anatomy, and wherein the mechanical strain includes bending.

7. The device of claim 1, wherein a portion of the heating element is outside of the piezoelectric patch.

8. The device of claim 1, wherein the heating element includes a metal susceptible to heating induced by magnetic resonance imaging (MRI).

9. The device of claim 8, wherein the heating element includes a coiled wire.

10. The device of claim 8, wherein the heating element includes a serpentine wire.

11. The device of claim 8 further comprising a drug delivery mechanism.

12. The device of claim 11, wherein the drug delivery mechanism includes a drug depot in the flexure area, the drug depot being filled with a drug.

13. The device of claim 12, wherein the drug depot is covered by a membrane.

14. The device of claim 12, wherein the flexure area includes a width, a length 1 to 20 times the width, and a thickness 0.01 to 0.15 times the width.

15. A method of treating a patient tissue comprising:
delivering a medical implant having a piezoelectric patch including a flexure area to undergo mechanical strain caused by a target anatomy, an anchor, and a heating element coupled to the piezoelectric patch, wherein the heating element is at least partially within the piezoelectric patch, and wherein the heating element is configured to generate heat in response to an oscillating electromagnetic field induced by an external source; and
securing the flexure area to the target anatomy at an intracorporeal site of a patient.

16. The method of claim 15, wherein the flexure area includes a poled PVDF polymer.

17. The method of claim 16 further comprising directing voltage generated within the flexure area to the target anatomy.

18. The method of claim 17 further comprising heating the target anatomy with heat generated in the heating element by external stimulation from the external source.

19. The method of claim 18, wherein the medical implant includes a drug delivery mechanism, and further comprising delivering a drug to the target anatomy from the drug delivery mechanism.

20. The method of claim 16, wherein the target anatomy includes muscle tissue.

21. The method of claim 20, wherein the target anatomy moves cyclically, and wherein the cyclic motion generates electricity in the flexure area.

22. The method of claim 15, wherein the flexure area is configured to undergo mechanical strain caused by the target anatomy.

* * * * *